US012569535B2

(12) United States Patent
Tran et al.

(10) Patent No.: US 12,569,535 B2
(45) Date of Patent: Mar. 10, 2026

(54) COMPOSITIONS AND METHODS FOR ENHANCING SYSTEMIC DELIVERABILITY, TOLERABILITY, AND EFFICACY OF CATIONIC MACROCYCLIC PEPTIDES

(71) Applicant: University of Southern California, Los Angeles, CA (US)

(72) Inventors: Dat Tran, Alhambra, CA (US); Justin Schaal, Orange, CA (US); Patti Tran, Alhambra, CA (US); Michael E. Selsted, Pasadena, CA (US)

(73) Assignee: University of Southern California, Los Angeles, CA (US)

( * ) Notice: Subject to any disclaimer, the term of this patent is extended or adjusted under 35 U.S.C. 154(b) by 738 days.

(21) Appl. No.: 17/283,384

(22) PCT Filed: Oct. 9, 2019

(86) PCT No.: PCT/US2019/055362
§ 371 (c)(1),
(2) Date: Apr. 7, 2021

(87) PCT Pub. No.: WO2020/076925
PCT Pub. Date: Apr. 16, 2020

(65) Prior Publication Data
US 2021/0346463 A1 Nov. 11, 2021

Related U.S. Application Data

(60) Provisional application No. 62/743,243, filed on Oct. 9, 2018.

(51) Int. Cl.
*A61K 38/12* (2006.01)
*A61K 47/10* (2017.01)

(52) U.S. Cl.
CPC .............. *A61K 38/12* (2013.01); *A61K 47/10* (2013.01)

(58) Field of Classification Search
CPC .... A61K 38/12; A61K 47/10; A61K 38/1709; A61K 9/0019; A61K 9/08; A61K 38/1729; A61K 47/14; A61P 1/00; A61P 19/02; A61P 29/00; C07K 14/4723; A61L 2/0017
See application file for complete search history.

(56) References Cited

U.S. PATENT DOCUMENTS

| | | | |
|---|---|---|---|
| 2004/0086535 A1 | 5/2004 | Maury et al. | |
| 2006/0084605 A1 | 4/2006 | Engelund et al. | |
| 2006/0287221 A1 | 12/2006 | Knudsen et al. | |
| 2007/0010424 A1 | 1/2007 | Pedersen et al. | |
| 2013/0157964 A1* | 6/2013 | Selsted .............. | C07K 14/4723 |
| | | | 514/21.1 |
| 2017/0035845 A1 | 2/2017 | Selsted et al. | |

FOREIGN PATENT DOCUMENTS

| | | | | |
|---|---|---|---|---|
| CN | 102784386 | 11/2012 | | |
| CN | 103732239 | 4/2014 | | |
| JP | 2014516990 A | 7/2014 | | |
| JP | 2014523906 A | 9/2014 | | |
| JP | 2014516990 | 8/2017 | | |
| JP | 2014523906 | 10/2017 | | |
| KR | 20140053911 | 5/2014 | | |
| RU | 98102443 A | 11/1999 | | |
| WO | 2005049061 | 6/2005 | | |
| WO | WO-2005049061 A2 * | 6/2005 | ............. | A61K 38/26 |
| WO | 2006/052637 | 5/2006 | | |
| WO | 2012/167077 | 12/2012 | | |
| WO | 2013/007596 | 1/2013 | | |
| WO | 2015/198265 | 12/2015 | | |
| WO | WO-2016059593 A1 * | 4/2016 | ........... | A61K 38/166 |
| WO | 2018/108971 | 6/2018 | | |

OTHER PUBLICATIONS

Bowie et al (Science, 1990, 247:1306-1310) (Year: 1990).*
Burgess et al (J. Cell Biol. 111:2129-2138, 1990) (Year: 1990).*
Lazar et al (Mol. Cell. Biol., 8:1247-1252, 1988) (Year: 1988).*
Pharmaceuticals: pp. 405-435; Hanrimwon Limited Company, Mar. 20, 1995. 79 pages.
Ochiai, et al. "Analysis of apoptosis induction mechanism in antifungal defensin," Scientific Reports, 8, 11424. 2018. 4 pages.
Boniotto et al, Antimicrob Agents Chemother 50:1433-1441 (2006).
Chertov et al, J Biol Chem 271:2935-2940 (1996).
Ericksen et al, Antimicrob Agents Chemother 49:269-275 (2005).
Garcia et al, Infect Immun 76:5883-5891 (2001).
Grigat et al, J Immunol 179:3958-3965 (2007).
Ito et al, Tohoku J Exp Med 227:39-48 (2012).
Khine et al, Blood 107:2936-2942 (2006).
Lehrer et al, J Biol Chem 287:27014-27019 (2012).
Leonova et al, J Leukoc Biol 70:461-464 (2001).
Li et al, Invest Ophthalmol Vis Sci 50:644-653 (2009).

(Continued)

*Primary Examiner* — Sudhakar Katakam
(74) *Attorney, Agent, or Firm* — FISH IP LAW, LLP

(57) ABSTRACT

Compositions are provided for formulations of θ-defensin and/or a θ-defensin analog that are highly suitable for parenteral administration. Such formulations provide the θ-defensin and/or a θ-defensin analog in a slightly acidic buffer that includes propylene glycol. Surprisingly, Inventors have found that such formulation increase bioavailability of a θ-defensin and/or a θ-defensin analog so provided by at least a factor of 10 relative to conventional isotonic saline solutions, and that such formulations dramatically improved bioavailability in human subjects relative to animal models. Inventors have also found that such formulations advantageously exhibit low viscosity at high peptide concentrations, reducing injection volume permitting sterilization by simple filtration.

11 Claims, 15 Drawing Sheets
Specification includes a Sequence Listing.

(56)                    References Cited

OTHER PUBLICATIONS

Nguyen et al, Peptides 24:1647-1654 (2003).
Niyonsaba et al, J Immunol 175:1776-1784 (2005).
Schaal et al, PLoS One 7, e51337 (2012).
Selsted and Ouellette, Nat Immunol 6:551-557 (2005).
Soruri et al, Eur J Immunol 37:2474-2486 (2007).
Syeda et al, J Cell Physiol 214:820-827 (2008).
Tang et al, Science 286:498-502 (1999).
Tongaonkar et al, J Leukoc Biol 89:283-290 (2011).
Wohlford-Lenane et al, J Virol 83:11385-11390 (2009).
Yang et al, Science 286:525-528 (1999).
Yang et al, Annu Rev Immunol 22:181-215 (2004).
Yin et al, Immunol 11:37. (2010).
Michael Selsted et al., "Use of Naturally Occurring Cyclic Peptides for Treatment of SARS-COV-2 Infection", co-pending U.S. Appl. No. 18/273,181, dated Jul. 19, 2023, 57 pages.
Michael Selsted et al., "Novel Theta Defensin Analogs and Methods of Use", co-pending U.S. Appl. No. 18/914,690, dated Oct. 14, 2024, 25 pages.
Michael Selsted et al., "Compositions and Methods for Treatment of Fungal Infections", co-pending U.S. Appl. No. 18/914,161, dated Oct. 12, 2024, 37 pages.
Michael Selsted et al., "Compositions and Methods for Treatment of Fungal Infections", co-pending U.S. Appl. No. 18/670,613, dated May 21, 2024, 25 pages.
Michael Selsted et al., "Methods for Enhancing Immune Check-point Inhibitor Therapy", co-pending U.S. Appl. No. 18/669,253, dated May 21, 2024, 44 pages.
Michael Selsted et al., "Compositions and Methods for Treatment of Protease Mediated Disease", co-pending U.S. Appl. No. 18/961,498, dated Nov. 27, 2024, 37 pages.
Michael Selsted et al., "Compositions and Methods for Treatment of Fungal Infections", co-pending U.S. Appl. No. 17/948,904, dated Sep. 20, 2022, 55 pages.
Michael Selsted et al., "Prophylactic Uses of Theta Defensins", co-pending U.S. Appl. No. 18/706,707, dated May 1, 2024, 44 pages.
Jakubke, et al., "Amino acids Peptides, Proteins", Moscow "Peace", dated 1985, pp. 92-94.
Intenrational Search Report for International Patent Application PCT/2019/055362, dated Jan. 20, 2020, 4 pages.
Akihito Ochiai et al., "Japan Society for Bioscience, Biotechnology, and Agrochemistry, The 2020 Annual Meeting Presentation No. 2B04p04, Analysis of apoptosis induction mechanism in antifungal defensin", transcript, dated Mar. 26, 2020, 1 page.
Angie E Garcia et al. Isolation, synthesis, and antimicrobial activities of naturally occurring theta-defensin isoforms from baboon leukocytes. Infect Immun. Dec. 2008;76(12):5883-91, dated Oct. 13, 2008, 9 pages.

* cited by examiner

Male rats          Female rats

Male rats          Female rats

Male rats

Female rats

Male rats

Female rats

COMPOSITIONS AND METHODS FOR ENHANCING SYSTEMIC DELIVERABILITY, TOLERABILITY, AND EFFICACY OF CATIONIC MACROCYCLIC PEPTIDES

This application claims the benefit of U.S. Provisional Application No. 62/743,243, filed on Oct. 9, 2018. These and all other referenced extrinsic materials are incorporated herein by reference in their entirety. Where a definition or use of a term in a reference that is incorporated by reference is inconsistent or contrary to the definition of that term provided herein, the definition of that term provided herein is deemed to be controlling.

This invention was made with government support under Grant No. 1R44AR068833-01, awarded by the National Institute of Arthritis and Musculoskeletal and Skin Diseases (NIH/NIAMS). The government, has certain rights in the invention.

FIELD OF THE INVENTION

The field of the invention is enhancement of systemic deliverability or pharmacologic effect of cationic peptide drugs, in particular enhancement of macrocyclic θ-defensins and/or analogs thereof.

BACKGROUND

The following description includes information that may be useful in understanding the present invention. It is not an admission that any of the information provided herein is prior art or relevant to the presently claimed invention, or that any publication specifically or implicitly referenced is prior art.

Inflammation is a complex protective response to pathogens, tissue damage, and exposure to irritants, involving alteration in blood vessels, mobilization of immune cells, and release of a variety of chemical and peptide mediators. While inflammation serves to remove the initial cause of cell injury and eliminate necrotic cells from damaged tissue, the inflammatory response can itself be damaging. For example, chronic inflammation resulting from autoimmune disease can contribute to damage of the affected tissue. Similarly, inflammation resulting from acute processes, such as viral or bacterial infection, can result in tissue damage and septic shock, and this may be exacerbated by chronic inflammation when the initial insult results in prolonged and unresolved inflammation. Chronic inflammation often leads to tissue scarring, fibrosis, and loss of function. In addition, the pain and swelling that accompany inflammation can be debilitating, particularly when it is the result of chronic conditions.

Unfortunately, current methods for treating inflammation suffer from a number of drawbacks. For example, traditional pharmaceutical approaches (e.g. treatment with steroids or non-steroidal inflammatory drugs) provide only short term relief, and often do so at the cost of significant side effects that limit the use of such drugs. More recently, "biologics" (for example, humanized monoclonal antibodies to proinflammatory cytokines) have been used to treat certain chronic conditions characterized by inflammation, however such approaches necessarily target only a single inflammation mechanism, and can result in immune suppression or even an immunocompromised state in a treated individual. In addition, antibody-based biologics can require the intravenous administration of relatively large volumes of fluid, which is generally administered by infusion while under the care of trained medical personnel.

Mammalian defensins are cationic, tri-disulfide-containing peptides comprising three structurally distinct and different subfamilies. The α and β defensins are linear peptides that range in length from 29 to about 60 amino acids, with free amino and carboxyl terminal amino acids. The α- and β-defensins have similar three dimensional topologies but differ in their disulfide linkages (Selsted and Ouellette, Nat Immunol 6:551-557 (2005)). In contrast, naturally occurring θ-defensins are peptide backbone-cyclized 18-amino acid peptides that are both structurally and functionally distinct from α and β defensins. Defensins contribute to host defense as antimicrobial agents (Ericksen et al, Antimicrob Agents Chemother 49:269-275 (2005)) and by regulating inflammatory (Khine et al, Blood 107:2936-2942 (2006)) and adaptive immune responses (Chertov et al, J Biol Chem 271:2935-2940 (1996)). All publications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

θ-defensins are expressed in Old World monkeys (e.g., macaques and baboons), and are the only known cyclic proteins in animals (Lehrer et al, J Biol Chem 287:27014-27019 (2012)). The basic θ-defensin backbone structure is produced by head-to-tail splicing of two nonapeptide precursors. In rhesus macaques alternate binary splicing of nonapeptides encoded by three precursor genes provides six θ-defensin isoforms, rhesus theta-defensins RTD-1 to RTD-6 (SEQ ID NOs. 1 to 6) (Tang et al, Science 286:498-502 (1999); Leonova et al, J Leukoc Biol 70:461-464 (2001)). In baboons, alternate nonapeptide splicing produces ten θ-defensin isoforms, baboon theta defensins BTD-1 to BTD-10 (SEQ ID Nos. 7 to 16) (Garcia et al, Infect Immun 76:5883-5891 (2001)). θ-defensins are expressed at high levels in granules of neutrophils and in monocytes of these species. These θ-defensins play a major role in the antimicrobial activities of rhesus neutrophil granule extracts. The RTD-1 isoform is the most abundant θ-defensin in macaques, constituting approximately 55% of the total θ-defensin content of rhesus neutrophils (Tongaonkar et al, J Leukoc Biol 89:283-290 (2011)).

Humans and other hominids lack θ-defensins due to the presence of a stop codon mutation in the prepro-coding sequence of θ-defensin genes in these species (Nguyen et al, Peptides 24:1647-1654 (2003)). It has been suggested that the expression of θ-defensins in Old World monkeys is related to differences in immune and inflammatory responses of these nonhuman primates from those of humans (Lehrer et al, J Biol Chem 287:27014-27019 (2012)).

While α-, β-, and θ-defensins were initially identified on the basis of broad spectrum antimicrobial properties, subsequent studies have disclosed different and distinct immune regulatory roles (Yang et al, Annu Rev Immunol 22:181-215 (2004)). For example, some α- and β-defensins are chemotactic for T cells, neutrophils, dendritic cells, and monocytes (Chertov et al, J Biol Chem 271:2935-2940 (1996); Yang et al, Science 286:525-528 (1999); Grigat et al, J Immunol 179:3958-3965 (2007); Soruri et al, Eur J Immunol 37:2474-2486 (2007)), and induce secretion of proinflammatory cytokines from activated dendritic cells, peripheral blood mononuclear cells and epithelial cells (Khine et al, 107: 2936-2942 (2006); Boniotto et al, Antimicrob Agents Chemother 50:1433-1441 (2006); Ito et al, Tohoku J Exp Med 227:39-48 (2012); Yin et al, Immunol 11:37. (2010); Niyonsaba et al, J Immunol 175:1776-1784 (2005); Li et al, Invest Ophthalmol Vis Sci 50:644-653 (2009); Syeda et al, J Cell Physiol 214:820-827 (2008)).

In contrast to such pro-inflammatory activities, it has recently been reported that θdefensins have anti-inflammatory properties both in vitro and in vivo. For example, RTD-1 was found to be a potent inhibitor of cytokine secretion by human peripheral blood leukocytes stimulated with diverse Toll-like receptor (TLR) agonists (Schaal et al, PLoS One 7, e51337 (2012)). Naturally occurring θ-defensin isoforms (RTDs 1 to 6) possess variable potency in reducing TNF in lipopolysaccharide- or *E. coli*-stimulated leukocytes. (Schaal et al, PLoS One 7, e51337 (2012)). RTD-1 has also been found to reduce inflammatory cytokines, including TNF-α, IL-1β, and several chemokines in mouse models of SARS coronavirus infection (Wohlford-Lenane et al, J Virol 83:11385-11390 (2009), in *E. coli* peritonitis, and in polymicrobial sepsis (Schaal et al, PLoS One 7, e51337 (2012)).

Recently, Selsted and Tran (United States Patent Application Publication No. 2013/0157964) have shown that θ-defensins and θ-defensin analogs that retain θ-defensin core structures are effective in treating chronic inflammatory conditions, such as rheumatoid arthritis. It is unclear, however, what formulations of these small cyclic peptides are optimal for achieving therapeutic efficacy at drug exposure low enough to limit potential adverse events, including those associated with injection site reactions following subcutaneous administration.

International Patent Application Publication No. WO 02/064166, to Jeong et al., describes a method for improving pharmacodynamic effect of some peptide drugs by forming an emulsion in the presence of a surfactant and an organic solvent in an aqueous solution, then removing the organic solvent prior to administration. Various alcohols and polyols, including propylene glycol, are cited as suitable organic solvents that are removed prior to administration. It is not clear, however, if this approach would be effective with a small, basic, cyclic peptide such as a θ-defensin.

United States Patent Application Publication No. 2006/084605 (to Engelud et al.) and United States Patent Application Publication No. 2006/0287221 (to Knudsen et al.) describe the use of various polyols in peptide pharmaceutical formulations for parenteral administration as isotonicity agents. Similarly, United States Patent Application Publication No. 2007/0010424 (to Pedersen et al.) describes the use of propylene glycol in place of various sugars as an isotonicity agent, in order to prevent the formation of deposits that can interfere with the function of equipment and needles utilized in the administration of various specified peptide drugs. The reference, however, does not document any effect beyond the reduction in solid residue provided by such formulations, and there is no evidence or suggestion that the use of such compounds had any effect on the bioavailability or pharmacodynamic effects of the peptide drugs so prepared.

International Patent Application Publication No WO 2016/059593 (to Sonavaria et al.) describes injectable formulations for peptide drugs that contain high (up to 99%) concentrations of organic solvents (including polyols), which are described as improving the stability of the peptides. Injection of high concentrations of such organic solvents, however, is associated with significant negative effects, including pain and swelling.

Thus, there is still a need for methods and compositions that provide a pharmacodynamic effect for administered defensins adequate to achieve sufficient therapeutic effect.

SUMMARY OF THE INVENTION

The inventive subject matter provides compositions and methods that provide injectable formulations for θ-defensins and θ-defensin analogs, and which provide improved bioavailability relative to conventional isotonic saline solutions. Such formulations also have low viscosity, permitting scalable sterilization by filtration.

One embodiment of the inventive concept is a method of treating an individual with a chronic inflammatory condition (such as rheumatoid arthritis, inflammatory bowel disease, inflammation associated with cancer, diabetes, and/or a chronic disease characterized by dysregulated or unresolved chronic inflammation) by providing a θ-defensin or θ-defensin analog as an aqueous solution comprising the θ-defensin or θ-defensin analog and from 0.5% to 1.5% v/v propylene glycol and having a pH of from 5.0 to 7.0, and administering the aqueous solution by subcutaneous injection to an individual in need of treatment. In some embodiments the aqueous solution includes an acetate salt. The aqueous solution provides an increase in pharmacologic potency or therapeutic effect of the θ-defensin or θ-defensin analog relative to a solution of the θ-defensin or θ-defensin analog in normal saline. The pharmacodynamic effect of the θ-defensin or θ-defensin analog can be increased by at least 10-fold to 40-fold relative to a similar concentration of the θ-defensin or θ-defensin analog provided in a normal saline solution. The θ-defensin or θ-defensin analog can be provided at concentrations up to 50 mgmL$^{-1}$. A θ-defensin analog utilized in the method can be a cyclic icosipeptide, a cyclic enneadecapeptide, a cyclic octadecapeptide, a cyclic heptadecapeptide, a cyclic hexadecapeptide, a cyclic pentadecapeptide, a cyclic tetradecapeptide, a cyclic tridecapeptide, a cyclic dodecapeptide, a cyclic hendecapeptide, or a cyclic decapeptide. In a preferred embodiment the aqueous solution includes 1% v/v propylene glycol and 20 mM acetate, and has a pH of 6.0.

Another embodiment of the inventive concept is a method of sterilizing an aqueous θ-defensin preparation by providing a θ-defensin or θ-defensin analog in an aqueous buffer that includes the θ-defensin or θ-analog at a concentration of at least 1 mgmL$^{-1}$ to 50 mgmL$^{-1}$ (or higher) and propylene glycol at from 0.5% to 1.5% v/v, and passing the aqueous buffer through a filter having a pore size of 0.2 μm or less. The aqueous buffer can include an acetate salt, and the resulting θ-defensin preparation can have a pH of 5.0 to 7.0.

Another embodiment of the inventive concept is a pharmaceutical composition for treatment of a chronic inflammatory condition (such as rheumatoid arthritis, inflammatory bowel disease, inflammation associated with cancer, diabetes, and/or a chronic disease characterized by dysregulated or unresolved chronic inflammation) that includes a θ-defensin or θ-defensin analog at up to 50 mgmL$^{-1}$ and propylene glycol at from 0.5% to 1.5% v/v, and can include an acetate salt. The pharmaceutical composition can have a pH of from 5.0 to 7.0 and provides an increase in pharmacodynamic effect of the θ-defensin or θ-defensin analog relative to a corresponding pharmaceutical composition prepared without propylene glycol on parenteral administration. The pharmacologic potency of the θ-defensin or θ-defensin analog is increased by at least 10-fold to 40-fold relative to an identical concentration of the θ-defensin or θ-defensin analog provided in a normal saline solution. Such a pharmaceutical composition can be formulated for subcutaneous injection, intramuscular injection, and/or intravenous injection. A suitable θ-defensin analog can be a cyclic icosipeptide, a cyclic enneadecapeptide, a cyclic octadecapeptide, a cyclic heptadecapeptide, a cyclic hexadecapeptide, a cyclic pentadecapeptide, a cyclic tetradecapeptide, a cyclic tridecapeptide, a cyclic dodecapeptide, a cyclic hendecapeptide, or a cyclic decapeptide. In a preferred embodiment the pharmaceutical composition includes 1% v/v propylene glycol and 20 mM acetate, and has a pH of 6.0.

Another embodiment of the inventive concept is the use of a θ-defensin or θ-defensin analog at a concentration of up to 50 mgmL$^{-1}$ and in a solution containing propylene glycol at from 0.5% to 1.5% v/v for treatment of a chronic inflammatory condition (such as rheumatoid arthritis, inflammatory bowel disease, inflammation associated with cancer, diabetes, and/or a chronic disease characterized by dysregulated or unresolved chronic inflammation). The solution can include an acetate salt. The solution is formulated for parenteral administration, can have a pH of from 5.0 to 7.0, and provides increased pharmacodynamic effect of the θ-defensin or θ-defensin analog relative to a corresponding amount of θ-defensin or θ-defensin analog prepared without propylene glycol. Pharmacologic potency of the θ-defensin or θ-defensin analog can be increased by at least 10-fold to 40-fold on parenteral administration relative to a similar concentration of the θ-defensin or θ-defensin analog provided in a normal saline solution. Suitable routes for parenteral administration include subcutaneous injection, intramuscular injection, and/or intravenous injection. Suitable θ-defensin analogs include a cyclic icosipeptide, a cyclic enneadecapeptide, a cyclic octadecapeptide, a cyclic heptadecapeptide, a cyclic hexadecapeptide, a cyclic pentadecapeptide, a cyclic tetradecapeptide, a cyclic tridecapeptide, a cyclic dodecapeptide, a cyclic hendecapeptide, and/or a cyclic decapeptide. In a preferred embodiment the composition includes 1% v/v propylene glycol and 20 mM acetate, and has a pH of 6.0.

Another embodiment of the inventive concept is use of a θ-defensin or θ-defensin analog at up to 50 mgmL$^{-1}$ and propylene glycol at from 0.5% to 1.5% v/v for preparation of a composition useful for treatment of a chronic inflammatory condition (such as rheumatoid arthritis, inflammatory bowel disease, inflammation associated with cancer, diabetes, and/or a chronic disease characterized by dysregulated or unresolved chronic inflammation). The solution can include an acetate salt. The composition is formulated for parenteral administration, can have a pH of from 5.0 to 7.0, and provides increased pharmacodynamic effect of the θdefensin or θ-defensin analog relative to a corresponding amount of θ-defensin or θ-defensin analog prepared without propylene glycol. Pharmacologic potency of the θ-defensin or θdefensin analog can be increased by at least 10-fold to 40-fold on parenteral administration relative to a similar concentration of the θ-defensin or θ-defensin analog provided in a normal saline solution. Suitable routes for parenteral administration include subcutaneous injection, intramuscular injection, and/or intravenous injection. Suitable θ-defensin analogs include a cyclic icosipeptide, a cyclic enneadecapeptide, a cyclic octadecapeptide, a cyclic heptadecapeptide, a cyclic hexadecapeptide, a cyclic pentadecapeptide, a cyclic tetradecapeptide, a cyclic tridecapeptide, a cyclic dodecapeptide, a cyclic hendecapeptide, and/or a cyclic decapeptide. In a preferred embodiment the composition includes 1% v/v propylene glycol and 20 mM acetate, and has a pH of 6.0.

Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWINGS

FIG. 1 shows typical data demonstrating the effects of subcutaneous injection of RTD-1 in saline on an animal model of rheumatoid arthritis.

FIG. 2 shows typical effects of subcutaneous injection of RTD-1 in saline containing 1% (v/v) propylene glycol on an animal model of rheumatoid arthritis.

FIG. 3 shows typical effects of subcutaneous injection of RTD-1 in saline containing 1% (v/v) propylene glycol or 20 mM Na acetate containing 1% (v/v) propylene glycol on an animal model of rheumatoid arthritis.

FIGS. 4A and 4B show graphs of plasma θ-defensin concentration (in ng/mL) vs time (in hours) for male and female rats, respectively, on day 1 of a study in which a θ-defensin formulation of the inventive concept is injected subcutaneously.

FIGS. 5A and 5B show graphs of plasma θ-defensin concentration (in ng/mL) vs time (in hours) for male and female rats, respectively, on day 13 of a study in which a θ-defensin formulation of the inventive concept is injected subcutaneously.

FIGS. 6A and 6B show graphs of plasma θ-defensin concentration (in ng/mL) vs time (in hours) for male and female rats, respectively, on day 41 of a study in which a θ-defensin formulation of the inventive concept is injected subcutaneously.

FIG. 7A provides a graph depicting results of a $C_{max}$ vs. θ-defensin dose linearity study for male and female rats at day 1 of a study in which a θ-defensin formulation of the inventive concept is injected subcutaneously. FIG. 7B provides a graph depicting results of a $C_{max}$ vs. θ-defensin dose linearity study for male and female rats at day 41 of a study in which a θ-defensin formulation of the inventive concept is injected subcutaneously.

FIG. 8A provides a graph depicting results of an $AUC_{0-TLast}$ vs. θ-defensin dose linearity study for male and female rats at day 1 of a study in which a θ-defensin formulation of the inventive concept is injected subcutaneously. FIG. 8B provides a graph depicting results of an $AUC_{0-TLast}$ vs. θ-defensin dose linearity study for male and female rats at day 41 of a study in which a θ-defensin formulation of the inventive concept is injected subcutaneously.

FIG. 9 shows typical results for measurement of θ-defensin concentration (ng/mL) in plasma over time for different treatment groups in a human clinical trial in which a θ-defensin formulation of the inventive concept was injected subcutaneously.

FIG. 10A shows a typical dependence of $C_{max}$ (ng/mL) on dose (μg/kg) of a θ-defensin formulation of the inventive concept that was injected subcutaneously in a human clinical trial. FIG. 10B shows a typical dependence of $AUC_{0-TLast}$ on dose (μg/kg) of a θ-defensin formulation of the inventive concept that was injected subcutaneously in a human clinical trial.

FIG. 11A shows a typical dependence of $C_{max}$ (ng/mL) on total θ-defensin dose (mg) of a θ-defensin formulation of the inventive concept that was injected subcutaneously in a human clinical trial. FIG. 11B shows a typical dependence of $AUC_{0-TLast}$ on total θ-defensin dose (mg) of a θ-defensin formulation of the inventive concept that was injected subcutaneously in a human clinical trial.

DETAILED DESCRIPTION

Figure 1:
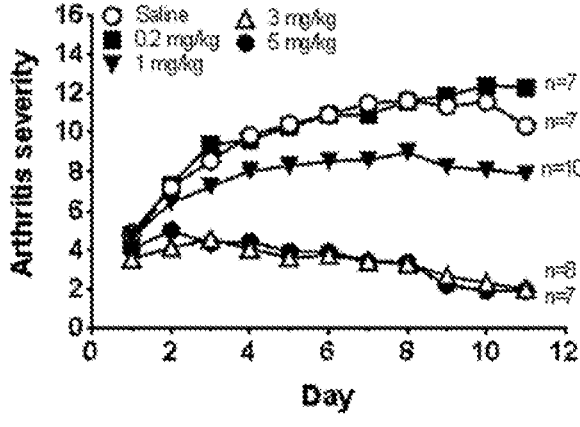
FIG. 1.

The following discussion provides many example embodiments of the inventive subject matter. Although each embodiment represents a single combination of inventive elements, the inventive subject matter is considered to include all possible combinations of the disclosed elements. Thus, if one embodiment comprises elements A, B, and C, and a second embodiment comprises elements B and D, then the inventive subject matter is also considered to include other remaining combinations of A, B, C, or D, even if not explicitly disclosed.

The inventive subject matter provides apparatus, systems and methods in which propylene glycol at from 0.5% to 1.5% in a slightly acidic (e.g. pH of 5 to 7) aqueous solution has, surprisingly, been found to increase the preclinical efficacy of a parenterally administered θ-defensin and/or θ-defensin analog by at least 20-fold relative to conventional neutral isotonic saline solutions. This permits convenient subcutaneous administration of θ-defensin in relatively small volumes (e.g. about 1 mL) in amounts that are effective in treating chronic inflammatory conditions such as rheumatoid arthritis, inflammatory bowel disease, or diabetes, or other conditions resulting from dysregulated inflammatory responses in humans. Addition of propylene glycol at these concentrations was also unexpectedly found to dramatically reduce the viscosity of concentrated (e.g. 10 $mgmL^{-1}$ or higher) solutions of θ-defensin, permitting simple, convenient, and scalable sterilization by filtration. Further, the formulation of θ-defensin markedly reduced injection site reactions relative to those observed when isotonic saline was used as the formulation vehicle.

Suitable θ-defensins include native θ-defensins found in mammals expressing these peptides, and can also include one or more θ-defensins derived from untranslated genes present in some primate species (e.g. *Homo sapiens*). In some embodiments of the inventive concept one or more θ-defensin can correspond to those found in *Macaca mulatta*, for example RTD-1 (SEQ ID NO. 1), RTD-2 (SEQ ID NO. 2), RTD-3 (SEQ ID NO. 3), RTD-4 (SEQ ID NO. 4), RTD-5 (SEQ ID NO. 5), and/or RTD-6 (SEQ ID NO. 6). In other embodiments of the inventive concept one or more θ-defensin can correspond to those found in *Papio anubis*, for example BTD-1 (SEQ ID NO. 7), BTD-2 (SEQ ID NO. 8), BTD-3 (SEQ ID NO. 9), BTD-4 (SEQ ID NO. 10), BTD-5 (SEQ ID NO. 11), and/or BTD-6 (SEQ ID NO. 12), BTD-7 (SEQ ID NO. 13), BTD-8 (SEQ ID NO. 14), BTD-9 (SEQ ID NO. 15), and/or BTD-10 (SEQ ID NO. 16).

Within this application embodiments describing θ-defensins and uses thereof are inclusive of θ-defensin analogs. The term θ-defensin analog refers to a cyclic peptide having about 40%, 50%, 60%, 70%, 80%, 90% or greater sequence identity with a native θ-defensin peptide sequence. A θ-defensin analog can incorporate one, two, three, or more core features of a native θ-defensin. Exemplary core features include cyclic structure, the presence of one, two, three, or more disulfide bonds within the peptide (e.g. between pairs of cysteines of the analog), having a positive charge when in solution under physiological conditions, and the presence of beta pleated sheet secondary structure. Such θ-defensin analogs can include 10, 11, 12, 13, 14, 15, 16, 17, 18, 19, 20, or more than 20 amino acids, and in some embodiments can incorporate non-naturally occurring amino acids. An analog of a θ-defensin can include one or more L-amino acid(s), one or more D-amino acid(s), and/or a mixture of L- and D-amino acids. In some embodiments non-peptide bonds can be utilized between adjacent amino acid residues of a θ-defensin analog. θ-defensin analogs can represent one or more deletion or substitution of amino acids of a native θ-defensin sequence. Such substitutions can be conservative (e.g. where the substituted amino acid(s) retain(s) charge, hydrophobicity, hydrophilicity, and/or steric properties of the native amino acid). In some embodiments θ-defensin analogs can include grafting or conjugation of non-peptide moieties, for example polyethylene glycol and/or other hydrophilic polymers, cell-receptor targeting moieties, and/or moieties that aid in processing/purification. Examples of suitable theta defensin analogs that are based on RTD-1 (SEQ ID NO. 1) are provided as SEQ ID NO. 17 (RTD-1-27), SEQ ID NO. 18 (RTD-1-28), and SEQ ID NO. 19 (RTD-1-29).

Figure 2:
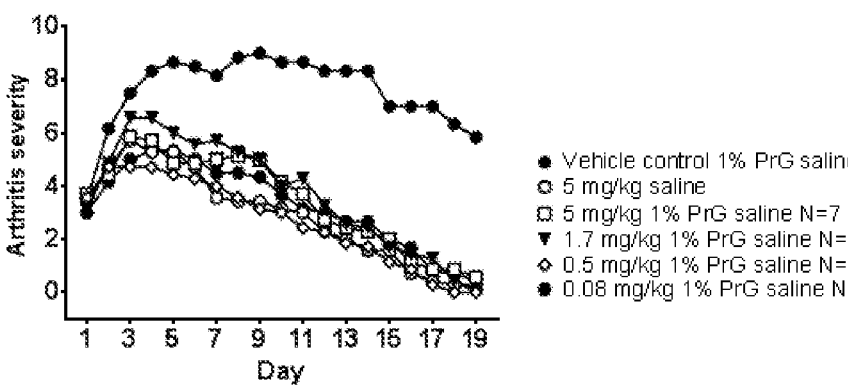
FIG. 2.
Figure 3:
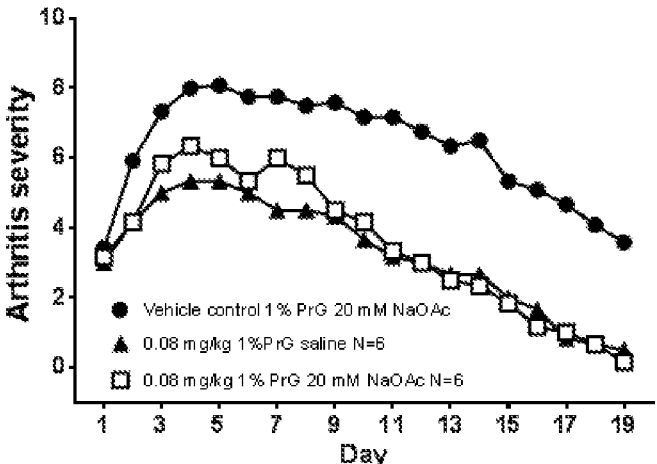
FIG. 3.

Compositions and methods for enhancing the pharmacologic effect of a θ-defensin and/or a θ-defensin analog utilized in the treatment of chronic inflammatory conditions (e.g. rheumatoid arthritis and/or diabetes) are provided herein. Such compositions incorporate from about 0.5% to about 1.5% propylene glycol in a mildly acidic aqueous solution (e.g. about pH 5 to 7), and are suitable for subcutaneous injection of θ-defensin at a concentration of up to 50 $mgmL^{-1}$. Such formulations have, surprisingly, been found to dramatically (e.g. greater than at least 10-fold) increase in pharmacologic effect or potency of the administered θ-defensin relative to θ-defensin provided at the same or similar concentrations in conventional saline solutions and/or solutions that do not include propylene glycol. This is shown in FIGS. 1, 2, and 3 below. It has also been found that such formulations have greatly reduced viscosity relative to θ-defensin provided in conventional normal saline solutions (e.g. phosphate buffered saline, pH 7 to 7.5) at similar concentrations, which permits sterilization by filtration. Further, compositions claimed markedly reduce injection site reactions compared to isotonic saline vehicle.

FIGS. 1, 2, and 3 show the results of treatment of an animal model of rheumatoid arthritis by subcutaneous injection of the θ-defensin RTD-1, where the θ-defensin is provided in either a conventional normal saline vehicle or in normal saline containing a low concentration (1% v/v) of propylene glycol. Rats with established pristane induced arthritis were treated with daily subcutaneous injections of RTD-1 formulated in normal saline at the indicated doses (FIG. 1) or in a saline solution containing 1% propylene glycol (FIG. 2). The lowest effective RTD-1 dose in the normal saline diluent was 1 mg/kg, with maximal apparent effect seen at 3 mg/kg (see FIG. 1). The inclusion of 1% propylene glycol in the vehicle markedly lowered the effective RTD-1 dose (to 0.08 mg/kg, see FIG. 2) in that 0.08 mg/kg (the lowest dose tested) produced a maximal anti-arthritic effect, equivalent to 3 mg/kg doses of RTD-1 in saline (i.e. the maximum observed effect). Equivalent improvement in pharmacologic effect was obtained when RTD-1 was formulated in a buffered (20 mM sodium acetate) aqueous diluent containing 1% propylene glycol (FIG. 3). The Applicant believes that similar effects can be achieved at lower doses of the θ-defensin.

Surprisingly, it has also been found that such formulations have greatly reduced viscosity relative to θ-defensin provided in conventional normal saline solutions (e.g. isotonic phosphate buffered saline, pH 7 to 7.5) at similar concentrations, which permits sterilization by filtration.

Inventors have previously noted that θ-defensins and θ-defensin analogs (for example, cyclic octadecapeptides and/or cyclic tetradecapeptides) have significant effects in reducing inflammation in animal models of chronic inflammatory disease, such as pristane-treated rats. θ-defensins are readily soluble in aqueous solutions. In initial studies the θ-defensin was prepared in conventional normal saline solutions and was readily administered by subcutaneous injection with no apparent systemic ill effects in mice, though at high θ-defensin concentrations fat necrosis in the subcutaneous tissue was observed. Similarly, in rat and canine animal models, low concentrations of θ-defensins were well tolerated systemically and locally. However, at higher concentrations, injections of θ-defensin in normal saline resulted in localized inflammation and swelling at the injection site in a dose-dependent manner. Swelling and inflammation were found to persist for weeks. Relatively high concentrations of θ-defensin (e.g. about 10 to 50 mgmL$^{-1}$), however, are likely to be necessary to provide the necessary θ-defensin dosage while maintaining volumes appropriate for subcutaneous injection in human therapy.

Microscopic studies of injection sites where θ-defensin had been administered in conventional saline solution showed localized inflammation and necrotic changes at injection sites of canine and porcine test subjects. Without wishing to be bound by theory, Inventors believe that θ-defensin may be interacting with components of the extracellular matrix found within the skin of some mammals at subcutaneous injection depths, causing it to precipitate and/or form precipitating complexes within this tissue layer. Studies of the interaction of RTD-1 with whole blood, blood plasma collected following treatment with anticoagulant, and serum indicate that the θ-defensin interacts with fibrinogen to form insoluble complexes. Inventors believe that θ-defensin may, therefore, be interacting with fibrinogen and/or fibrinogen-like proteins associated with the extracellular matrix.

Inventors found that use of hypotonic saline, addition of poloxamers, and the use of other conventional excipients failed to reduce or eliminate this θ-defensin induced injection site inflammation and tissue injury. Surprisingly, low concentrations of propylene glycol were effective in providing solubility for high concentrations (e.g. 10 mgmL$^{-1}$ or greater) of θ-defensin and also in reducing or preventing swelling and/or inflammation on subcutaneous injection of high concentrations of θ-defensin into susceptible species. Propylene glycol is freely miscible with water, available as a sterile liquid of pharmaceutical grade, and is generally recognized as safe. The effective range of propylene glycol concentrations for reduction and/or elimination of adverse reactions on injection of high concentrations of θ-defensin was found to be relatively narrow. In some embodiments the effective concentration of propylene glycol in water was found to be from about 0.4% to about 1.6% (v/v). In other embodiments the effective concentration of propylene glycol in water was found to be about 0.5% to about 1.5% (v/v). In a preferred embodiment the effective concentration of propylene glycol in water is about 1% (v/v).

Further studies showed that, surprisingly, results were further improved by using a propylene glycol/water solvent with mildly acidic pH (e.g. from about pH 5 to 7). In a preferred embodiment the pH of the propylene glycol/water solvent is about 6.0, and has a final osmolality of about 180 to 230 mOsmoles. The pH of the propylene glycol/water solvent can be maintained using a buffer species at low molarity (e.g. less than about 50 mM). Suitable buffer concentrations can, for example, range from 1 mM to 50 mM, 5 mM to 35 mM, 10 mM to 30 mM, or about 20 mM. Suitable buffer species can be salts of organic acids, such as acetate, citrate, malate, tartrate, HEPES, MES, etc. In other embodiments the buffer species can be a zwitterionic species having a suitable pKa. In a preferred embodiment the buffer species is an acetate salt (e.g. sodium acetate) at a concentration of about 20 mM, and provides a pH of about 6.0. Surprisingly, Inventors have found that the use of saline (e.g. NaCl) in even small (e.g. less than 50 mM) amounts results in adverse reactions to subcutaneous injection of θ-defensin. Preferred embodiments of the aqueous solvent system used for subcutaneous administration can exclude NaCl and similar salts.

Surprisingly, Inventors have found that θ-defensins are freely soluble in such acidic propylene glycol/water solvent systems, and that only transient dermal reactions are found following subcutaneous injections of RTD-1 in rats and dogs at concentrations of up to 12.5 mgmL$^{-1}$, and with only minor adverse effects at 50 mgmL$^{-1}$. This supports the estimated 10 mgmL$^{-1}$ concentration of θ-defensin expected as necessary for providing dosing adequate for human treatment.

As noted above, Inventors unexpectedly found that use of a propylene glycol/water solvent system, in addition to eliminating the inflammation associated with saline-based formulations, dramatically increases the pharmacologic potency of a θ-defensin administered subcutaneously relative to conventional saline formulations. The increase in preclinical efficacy in established pristane-induced arthritis in mildly acidic propylene glycol/water relative to similar amounts provided in conventional saline solutions can be at least 5-fold, 10-fold, 15-fold, 20-fold, 30-fold, 40-fold, 50-fold, or more. For example, subcutaneous injection of RTD-1 provided at 0.08 mg/kg in 1% propylene glycol+20 mM acetate, pH 6, was found to have an effect equivalent to the administration of RTD-1 at 3 mg/kg in isotonic saline in the relief of symptoms of rheumatoid arthritis. This suggests an increase in pharmacologic potency of at least 37-fold, however since the relief of symptoms provided was at the upper limit of the benefit afforded by θ-defensins administered in isotonic saline it is probable that the actual increase in pharmacodynamic effect is greater than 37-fold (e.g. greater than 40-fold, 50-fold, 70-fold, 100-fold, or higher). This advantageously reduces the amount of θ-defensin necessary to provide adequate treatment.

Sterilization of conventional solutions utilized for injection is commonly performed by filtration, for example using a filter having a pore size of 0.2 µm or less. This process is, however, problematic for protein drug solutions as such solutions are typically too viscous for efficient sterile filtration at the high protein concentrations that are desirable to provide small injection volumes. As used herein, such a viscous solution refers to a solution or dispersion in which the internal resistance to flow is so high that filtration is difficult or impossible (e.g. requiring pressures exceeding the burst pressure of the filtration membrane). The viscosity of such a viscous solution can be as high as 105 centipoise (cp) or higher. In one embodiment the viscosity of such a viscous solution is at least about 90 to about 95 cp. In another embodiment the viscosity of such a viscous solution is at least about 40 cp. In still another embodiment the viscosity of such a viscous solution is at least above the viscosity of water (i.e. above about 1.0 cP).

During the course of investigation Inventors found that, while θ-defensins are highly soluble, aqueous solutions can become highly viscous as protein concentration increases. In practice conventional saline solutions of 2% w/v θ-defensin or higher were found to be too viscous to permit sterilization by filtration at a reasonable and/or manufacturable scale. Surprisingly, similar solutions prepared in propylene glycol/water solvents have low viscosity at high (e.g. 2% w/v, 5% w/v, 10% w/v, or greater) θ-defensin concentrations. This permits simple and scalable sterilization of such preparations using conventional filtration through media having a pore size of about 0.2 μm or less.

Embodiments of the inventive concepts include methods of treating conditions associated with chronic inflammation by subcutaneous injection of a drug composition that includes one or more θ-defensin(s) in an acidic aqueous solution containing propylene glycol at from 0.5% to 1.5%. Suitable conditions include rheumatoid arthritis, inflammatory bowel disease, diabetes, and other conditions resulting from dysregulation inflammatory responses. The drug composition can include a single species of θ-defensin or two or more species of θ-defensins. The drug composition can be administered subcutaneously in a volume ranging from about 0.1 mL to about 2.5 mL, about 0.25 mL to about 2 mL, 0.5 mL to about 1.5 mL, or about 1 mL. The concentration of θ-defensin or total concentration of species of θ-defensins in the drug composition can range from about 1 mgmL$^{-1}$ to about 50 mgmL$^{-1}$, and is preferably about 12.5 mgmL$^{-1}$ or less. Concentration of θ-defensin and/or injection volume can be adjusted to provide a dose of from about 0.001 mg/kg to about 3 mg/kg, about 0.01 to about 1 mg/kg, or about 0.08 mg/kg.

In some embodiments the drug composition can include, in addition to one or more θ-defensin(s) and/or θ-defensin analog(s) and propylene glycol, additional therapeutic compounds. For example, the drug composition can include one or more steroids having an anti-inflammatory effect, nonsteroidal anti-inflammatory drug(s), antibody(ies) or antibody fragment(s) directed to a pro-inflammatory cytokine, and/or one or analgesic compound(s).

Such preparations of θ-defensin can be administered using any suitable schedule. Subcutaneous injections can be provided at a frequency of once a week, twice a week, three times a week, alternating days, daily, every 12 hours, every 8 hours, or every 6 hours, as necessary to establish or maintain a desired therapeutic effect. Length of treatment can range from about 1 week, about 2 weeks, about 4 weeks, about 8 weeks, about 12 weeks, about 16 weeks, about 20 weeks, about 6 months, about 12 months, about 18 months, about 24 months, or greater than 24 months, as necessary to establish or maintain a desired therapeutic effect. In some embodiments dosing with θ-defensin can be higher and/or more frequent during initial stages of treatment in order to establish remission or partial remission of symptoms, then reduced in terms of either or both of θ-defensin dose and/or frequency of administration in order to maintain the remission of symptoms.

EXAMPLES

Pharmacokinetic Studies in Rats

The θ-defensin RTD-1 was formulated in a mildly acidic buffer containing propylene glycol as described above, and administered subcutaneously to male and female Sprague-Dawley rats followed by determination of plasma levels of the θ-defensin. Rats received doses ranging from 1 to 4 mg/kg. Dose volume was held constant at 0.32 mL/kg; accordingly, concentration of the θ-defensin ranged from 3.125 to 12.5 mg/mL. Doses were administered three times per week for six weeks. Exemplary results are shown in Table 1 (which provides results for male rats) and Table 2 (which provides results for female rats). Table 1 and the following tables use the following acronyms:

AUC$_{0-Last}$ Area under the plasma concentration versus time curve from time 0 (pre-dose) to the last measurable concentration time point C$_{Last}$ Last plasma concentration measured above the limit of quantitation C$_{max}$ Maximum plasma concentration MRT$_{Last}$ Mean residence time up to the last time point when plasma concentrations of analyte were measured

T$_{Last}$ Time at which the last plasma concentration above the limit of quantification was measured T$_{max}$ Time of maximum concentration.

TABLE 1

| Group and Dose | Day | C$_{max}$ (ng/mL)[1] | T$_{max}$ (hr)[1] | AUC$_{0-TLast}$ (ng*hr/mL) | T$_{Last}$ (hr) | C$_{Last}$ (ng/mL) | MRT$_{Last}$ (hr) |
|---|---|---|---|---|---|---|---|
| 2) RTD-1 Low Dose (1 mg/kg/dose) | Day 1 | 14.951 | 12 | 159 | 12 | 14.951 | 6.4 |
| | Day 13 | 74.644 | 4.0 | 951 | 24 | 13.369 | 10.0 |
| | Day 41 | 164.846 | 12 | 2158 | 24 | 17.766 | 9.8 |
| 3) RTD-1 Mid Dose (2 mg/kg/dose) | Day 1 | 26.635 | 0.5 | 319 | 24 | 13.747 | 11.8 |
| | Day 13 | 29.429 | 0.5 | 512 | 24 | 23.851 | 12.6 |
| | Day 41 | 208.296 | 12 | 3462 | 24 | 80.526 | 10.8 |
| 4) RTD-1 High Dose (4 mg/kg/dose) | Day 1 | 28.403 | 0.5 | 451 | 24 | 22.182 | 12.7 |
| | Day 13 | 54.720 | 0.5 | 776 | 24 | 35.863 | 12.6 |
| | Day 41 | 435.68 | 24 | 8103 | 24 | 435.680 | 13.1 |

[1]The apparent C$_{max}$ and T$_{max}$ values were determined for blood sampling times between pre-dose and 24 hours post dosing. There was no blood sampling between 12 and 24 hours. On Day 41, one highest mean plasma concentration in the High Dose group was found at the 24-hour blood sampling time point, indicating that it was possible that T$_{max}$ was achieved between 12 and 24 hours.

TABLE 2

| Group and Dose | Day | C$_{max}$ (ng/mL)[1] | T$_{max}$ (hr)[1] | AUC$_{0-TLast}$ (ng*hr/mL) | T$_{Last}$ (hr) | C$_{Last}$ (ng/mL) | MRT$_{Last}$ (hr) |
|---|---|---|---|---|---|---|---|
| 2) RTD-1 Low Dose (1 mg/kg/dose) | Day 1 | 18.901 | 0.5 | 357 | 24 | 14.579 | 12.2 |
| | Day 13 | 97.675 | 24 | 1215 | 24 | 97.675 | 15.4 |
| | Day 41 | 176.959 | 0.5 | 2133 | 24 | 144.416 | 13.8 |
| 3) RTD-1 Mid Dose (2 mg/kg/dose) | Day 1 | 20.997 | 12 | 400 | 24 | 13.849 | 12.0 |
| | Day 13 | 37.786 | 24 | 636 | 24 | 37.786 | 14.4 |
| | Day 41 | 296.145 | 12 | 4675 | 24 | 127.434 | 11.5 |
| 4) RTD-1 High Dose (4 mg/kg/dose) | Day 1 | 37.129 | 12 | 743 | 24 | 36.851 | 13.6 |
| | Day 13 | 177.471 | 12 | 2364 | 24 | 51.198 | 11.5 |
| | Day 41 | 305.575 | 12 | 6138 | 24 | 263.958 | 12.6 |

[1]The apparent C$_{max}$ and T$_{max}$ values were determined for blood sampling times between pre-dose and 24 hours post dosing. There was no blood sampling between 12 and 24 hours. On Day 41, one highest mean plasma concentration in the High Dose group was found at the 24-hour blood sampling time point, indicating that it was possible that T$_{max}$ was achieved between 12 and 24 hours.

Figure 4A:
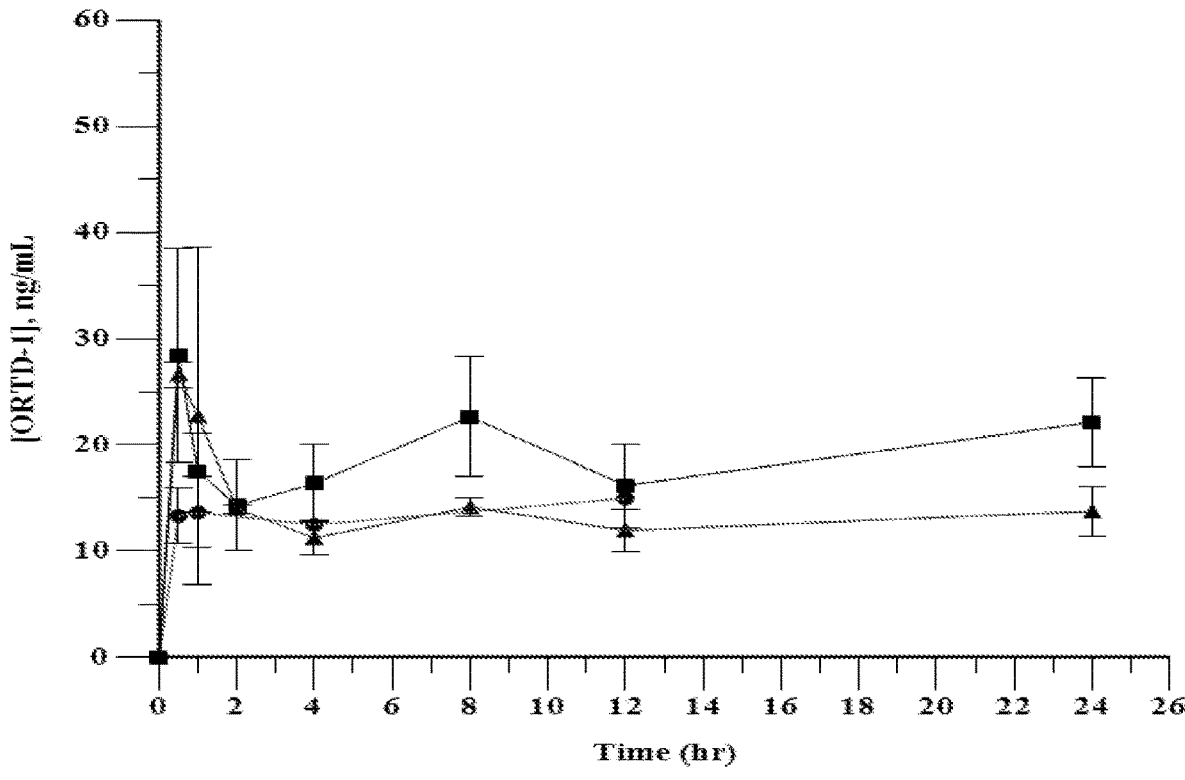
FIGS. 4A and 4B.
Figure 4B:
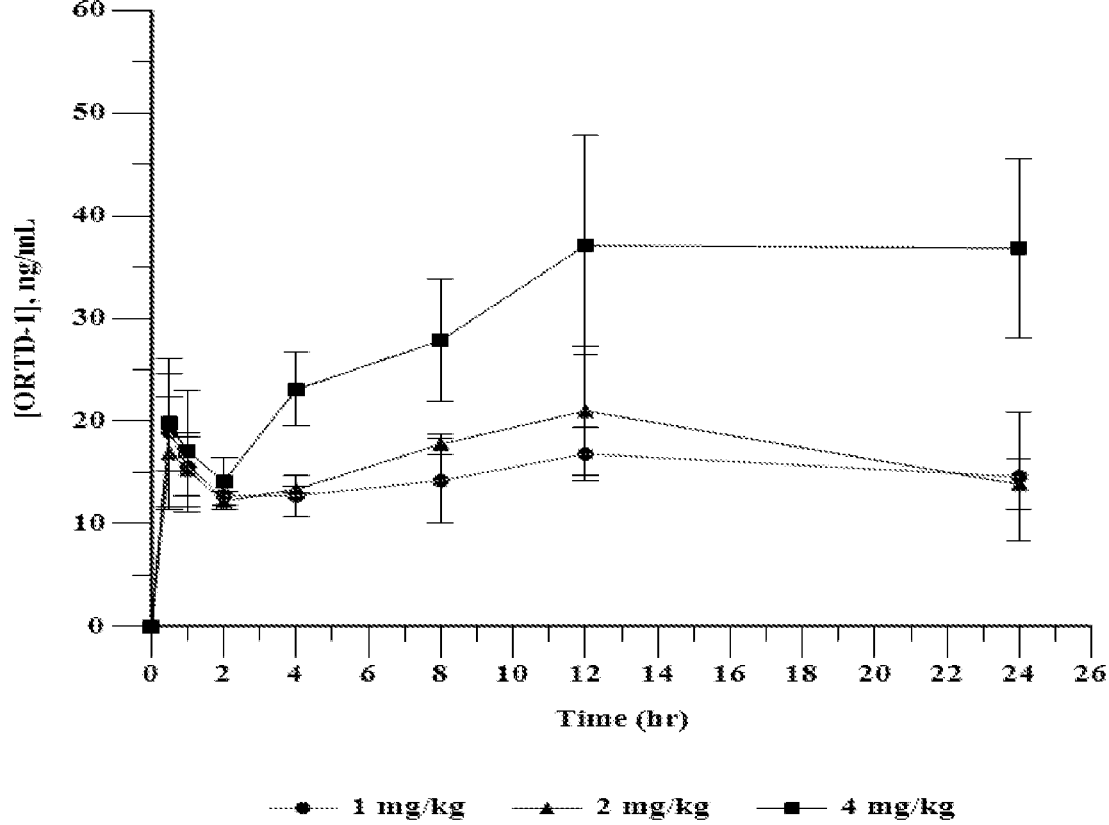
Figure 5A:
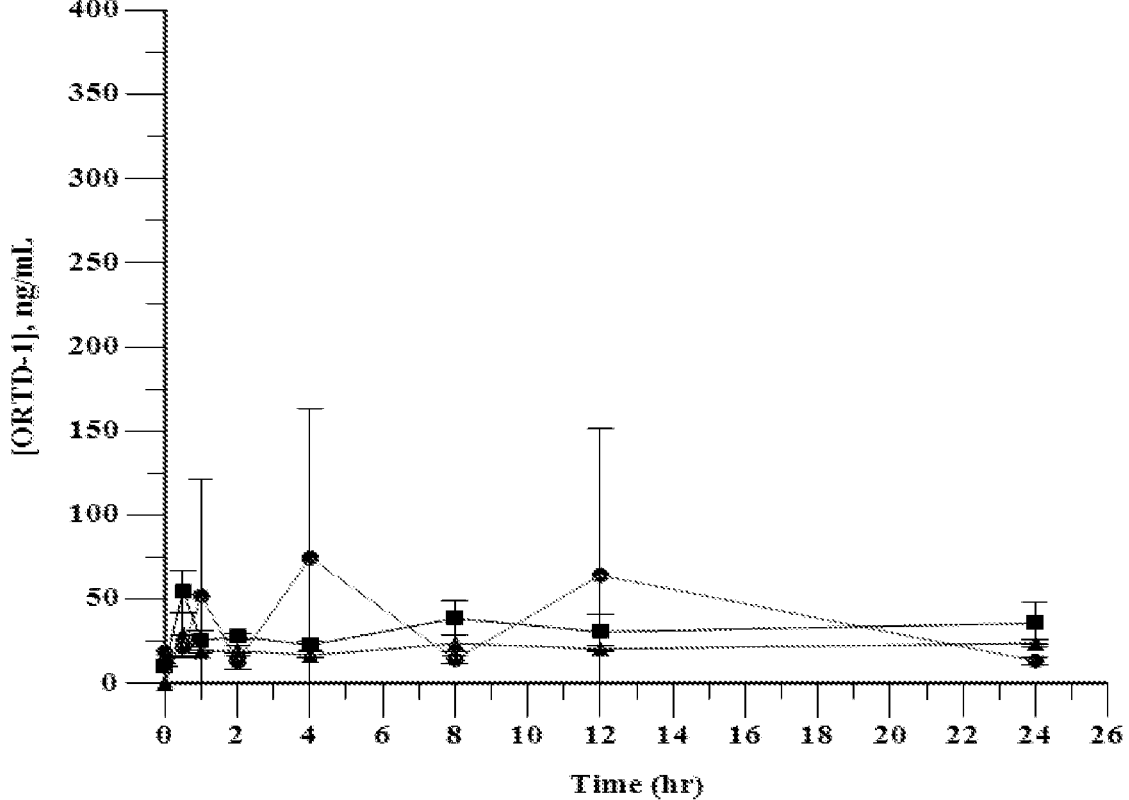
FIGS. 5A and 5B.
Figure 5B:
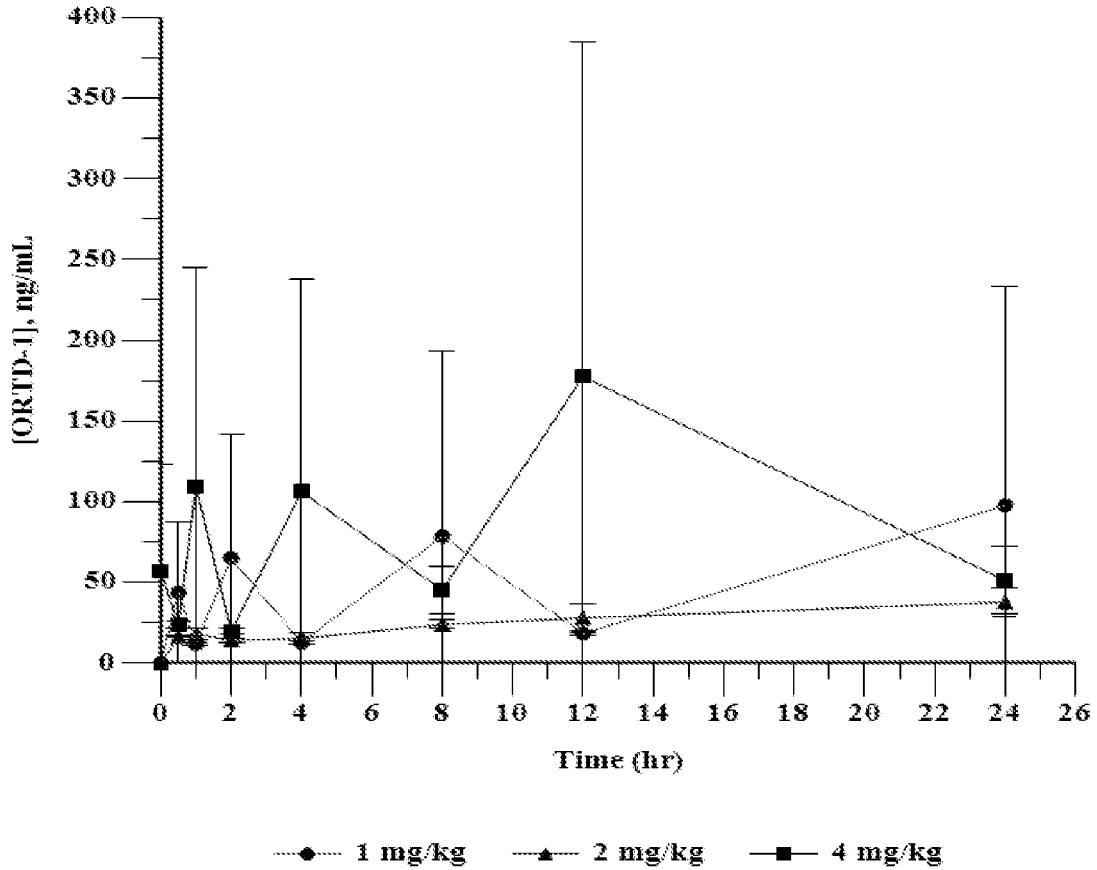
Figure 6A:
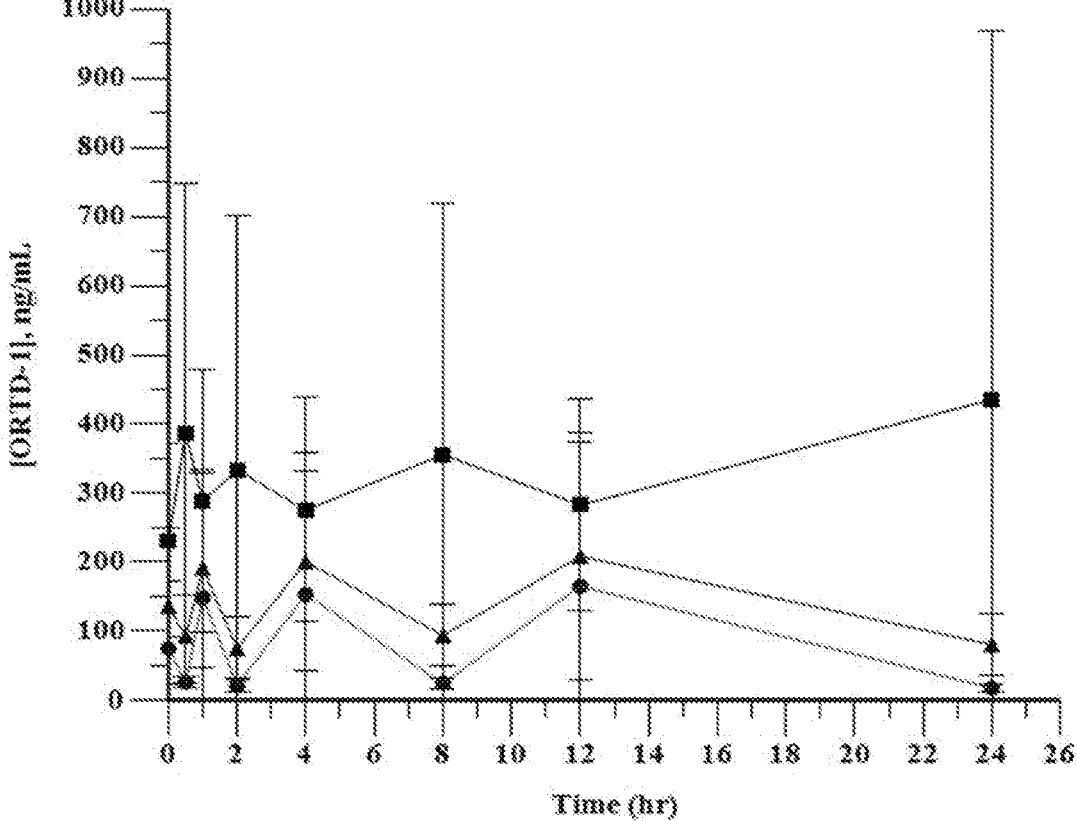
FIGS. 6A and 6B.
Figure 6B:
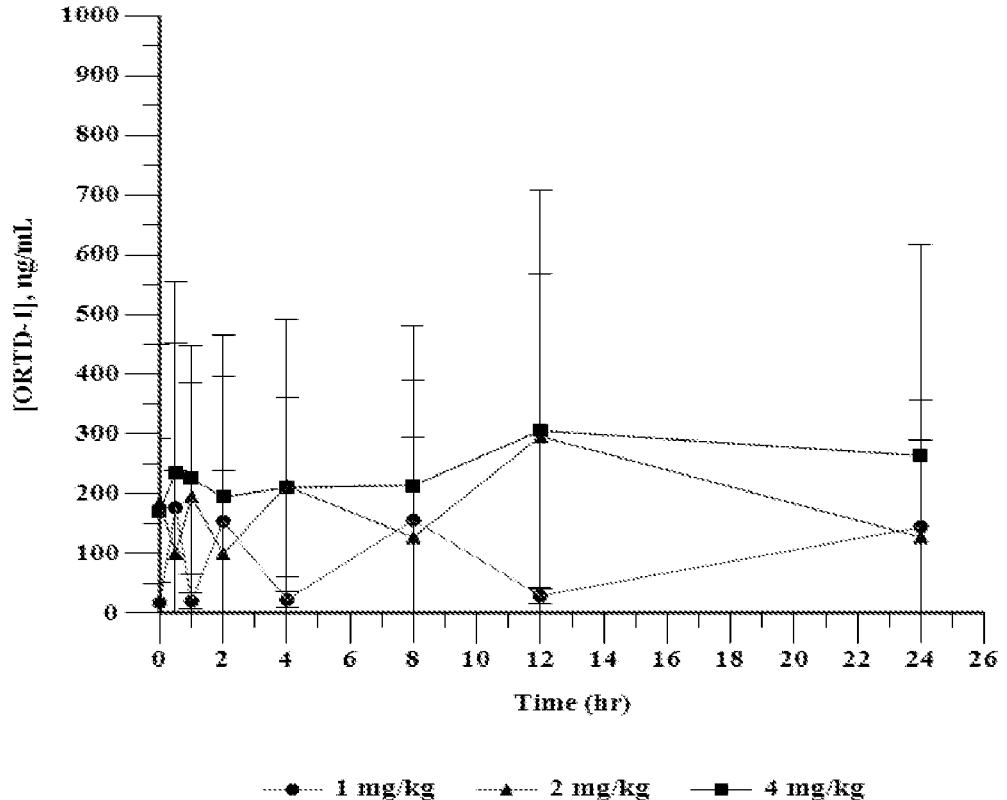

Tables 3, 4, and 5 show typical results from kinetic studies of plasma concentration of the θ-defensin (in ng/mL) in male rats receiving 1 mg/kg, 2 mg/kg, and 4 mg/kg, respectively. Tables 6, 7, and 8 show typical results from similar studies performed in female rats. FIGS. 4A and 4B show graphs of plasma θ-defensin concentration (in ng/mL) vs time (in hours) for male and female rats, respectively, on day 1 of such a study. FIGS. 5A and 5B show graphs of plasma θ-defensin concentration (in ng/mL) vs time (in hours) for male and female rats, respectively, on day 13 of such a study. FIGS. 6A and 6B show graphs of plasma θ-defensin concentration (in ng/mL) vs time (in hours) for male and female rats, respectively, on day 41 of such a study.

TABLE 3

| | | Sampling Time | | | | | | | |
| | | | | Time Post Dosing Relative to Pre-dose | | | | | |
| Group | | Pre-dose | 30 min | 1 hr | 2 hr | 4 hr | 8 hr | 12 hr | 24 hr |
|---|---|---|---|---|---|---|---|---|---|
| 2-TK RTD-1 | | | | | Day 1 | | | | |
| Low Dose | Mean | BLOQ | 13.302 | 13.614 | BLOQ | 12.464 | BLOQ | 14.951 | BLOQ |
| (1 mg/kg/dose) | SD | N/A | 2.630 | 3.329 | N/A | N/A | N/A | N/A | N/A |
| | % CV | N/A | 20 | 24 | N/A | N/A | N/A | N/A | N/A |
| | N* | 0 | 3 | 2 | 0 | 1 | 0 | 1 | 0 |
| | | | | | Day 13 | | | | |
| | Mean | 18.660 | 21.697 | 52.084 | 13.177 | 74.644 | 14.283 | 64.415 | 13.369 |
| | SD | N/A | 6.701 | 69.303 | 5.121 | 88.833 | 2.196 | 87.142 | 2.164 |
| | % CV | N/A | 31 | 133 | 39 | 119 | 15 | 135 | 16 |
| | N | 1 | 3 | 3 | 3 | 2 | 3 | 3 | 3 |
| | | | | | Day 41 | | | | |
| | Mean | 74.847 | 26.314 | 148.135 | 21.294 | 152.933 | 24.763 | 164.846 | 17.766 |
| | SD | 97.607 | 8.487 | 181.751 | 10.080 | 179.737 | 7.553 | 208.874 | 5.992 |
| | % CV | 130 | 32 | 123 | 47 | 118 | 31 | 127 | 34 |
| | N | 3 | 3 | 3 | 3 | 3 | 3 | 3 | 3 |

BLOQ—Below the limit of quantitation, <10 ng/mL; N represents the number of rats reporting with RTD-1 concentrations above the limit of quantitation.
Values are presented as the mean ± SD of N = 3 and the average ± the range of N = 2.
N/A—not applicable.

TABLE 4

| | | Sampling Time | | | | | | | |
| | | | | Time Post Dosing Relative to Pre-dose | | | | | |
| Group | | Pre-dose | 30 min | 1 hr | 2 hr | 4 hr | 8 hr | 12 hr | 24 hr |
|---|---|---|---|---|---|---|---|---|---|
| 3-TK RTD-1 | | | | | Day 1 | | | | |
| Mid Dose | Mean | BLOQ | 26.635 | 22.732 | 13.967 | 11.224 | 14.136 | 11.934 | 13.747 |
| (2 mg/kg/dose) | SD | N/A | 1.214 | 15.855 | 0.404 | 1.575 | 0.892 | 2.022 | 2.301 |
| | % CV | N/A | 5 | 70 | 3 | 14 | 6 | 17 | 17 |
| | N | 0 | 3 | 3 | 2 | 3 | 3 | 2 | 3 |
| | | | | | Day 13 | | | | |
| | Mean | BLOQ | 29.429 | 19.115 | 19.560 | 16.807 | 23.740 | 20.622 | 23.851 |
| | SD | N/A | 12.833 | 0.819 | 3.122 | 1.755 | 5.215 | 1.842 | 2.561 |
| | % CV | N/A | 44 | 4 | 16 | 10 | 22 | 9 | 11 |
| | N | 0 | 3 | 3 | 3 | 3 | 3 | 3 | 3 |
| | | | | | Day 41 | | | | |
| | Mean | 135.977 | 92.475 | 190.915 | 75.016 | 200.315 | 93.949 | 208.296 | 80.526 |
| | SD | 114.179 | 59.333 | 143.297 | 45.629 | 157.574 | 44.884 | 179.603 | 44.818 |
| | % CV | 84 | 64 | 75 | 61 | 79 | 48 | 86 | 56 |
| | N | 3 | 3 | 3 | 3 | 3 | 3 | 3 | 3 |

BLOQ—Below the limit of quantitation, <10 ng/mL; N represents the number of rats reporting with RTD-1 concentrations above the limit of quantitation.
Values are presented as the mean ± SD of N = 3 and the average ± the range of N = 2.
For N = 3, bold values are significantly different from Day 1; pair-wise comparison, $p < 0.05$ Student's t-test.
N/A—not applicable.

TABLE 5

| | | Sampling Time | | | | | | | |
| | | | | Time Post Dosing Relative to Pre-dose | | | | | |
| Group | | Pre-dose | 30 min | 1 hr | 2 hr | 4 hr | 8 hr | 12 hr | 24 hr |
|---|---|---|---|---|---|---|---|---|---|
| 4-TK RTD-1 | | | | | Day 1 | | | | |
| High Dose | Mean | BLOQ | 28.403 | 17.401 | 14.295 | 16.338 | 22.693 | 16.141 | 22.182 |
| (4 mg/kg/dose) | SD | N/A | 10.138 | 3.699 | 4.245 | 3.656 | 5.658 | 3.924 | 4.199 |
| | % CV | N/A | 36 | 21 | 30 | 22 | 25 | 24 | 19 |
| | N | 0 | 3 | 3 | 3 | 2 | 3 | 3 | 3 |
| | | | | | Day 13 | | | | |

TABLE 5-continued

| | | | | Time Post Dosing Relative to Pre-dose | | | | | |
| | | | | Sampling Time | | | | | |
| Group | | Pre-dose | 30 min | 1 hr | 2 hr | 4 hr | 8 hr | 12 hr | 24 hr |
|---|---|---|---|---|---|---|---|---|---|
| | Mean | 10.875 | 54.720 | 25.465 | 28.070 | 22.843 | 38.772 | 30.731 | 35.863 |
| | SD | 0.745 | 12.698 | 6.083 | 1.916 | 2.595 | 10.251 | 10.583 | 12.180 |
| | % CV | 7 | 23 | 24 | 7 | 11 | 26 | 34 | 34 |
| | N | 2 | 3 | 3 | 3 | 3 | 3 | 3 | 3 |
| | | | | | Day 41 | | | | |
| | Mean | 231.831 | 386.809 | 289.317 | 334.089 | 276.001 | 356.169 | 283.309 | 435.680 |
| | SD | 140.748 | 360.928 | 190.507 | 367.103 | 161.971 | 363.267 | 154.004 | 533.685 |
| | % CV | 61 | 93 | 66 | 110 | 59 | 102 | 54 | 122 |
| | N | 3 | 3 | 3 | 3 | 3 | 3 | 3 | 3 |

BLOQ—Below the limit of quantitation, <10 ng/mL; N represents the number of rats reporting with RTD-1 concentrations above the limit of quantitation.

Values are presented as the mean ± SD of N = 3 and the average ± the range of N = 2.

For N = 3, bold values are significantly different from Day 1; pair-wise comparison, $p < 0.05$ Student's t-test.

N/A—not applicable.

TABLE 6

| | | | | Time Post Dosing Relative to Pre-dose | | | | | |
| | | | | Sampling Time | | | | | |
| Group | | Pre-dose | 30 min | 1 hr | 2 hr | 4 hr | 8 hr | 12 hr | 24 hr |
|---|---|---|---|---|---|---|---|---|---|
| 2-TK RTD-1 | | | | | Day 1 | | | | |
| Low Dose | Mean | BLOQ | 18.901 | 15.549 | 12.780 | 12.731 | 14.212 | 16.814 | 14.579 |
| (1 mg/kg/dose) | SD | N/A | 7.198 | 2.879 | N/A | 1.960 | 4.152 | 2.611 | 6.260 |
| | % CV | N/A | 38 | 19 | N/A | 15 | 29 | 16 | 43 |
| | N | 0 | 3 | 3 | 1 | 3 | 2 | 3 | 3 |
| | | | | | Day 13 | | | | |
| | Mean | BLOQ | 43.692 | 11.859 | 65.055 | 12.849 | 78.536 | 18.469 | 97.675 |
| | SD | N/A | 43.430 | 0.935 | 76.310 | 1.092 | 114.621 | 1.051 | 136.032 |
| | % CV | N/A | 99 | 8 | 117 | 9 | 146 | 6 | 139 |
| | N | 0 | 3 | 3 | 2 | 2 | 3 | 3 | 3 |
| | | | | | Day 41 | | | | |
| | Mean | 17.879 | 176.959 | 20.237 | 154.096 | 22.465 | 156.429 | 29.272 | 144.416 |
| | SD | N/A | 274.447 | 13.515 | 243.129 | 12.674 | 233.247 | 12.116 | 212.016 |
| | % CV | N/A | 155 | 67 | 158 | 56 | 149 | 41 | 147 |
| | N | 1 | 3 | 3 | 3 | 3 | 3 | 3 | 3 |

BLOQ—Below the limit of quantitation, <10 ng/mL; N represents the number of rats reporting with RTD-1 concentrations above the limit of quantitation.
Values are presented as the mean ± SD of N = 3 and the average ± the range of N = 2.
N/A—not applicable.

TABLE 7

| | | | | Time Post Dosing Relative to Pre-dose | | | | | |
| | | | | Sampling Time | | | | | |
| Group | | Pre-dose | 30 min | 1 hr | 2 hr | 4 hr | 8 hr | 12 hr | 24 hr |
|---|---|---|---|---|---|---|---|---|---|
| 3-TK RTD-1 | | | | | Day 1 | | | | |
| Mid Dose | Mean | BLOQ | 16.871* | 15.297 | 12.222 | 13.357 | 17.759* | 20.997 | 13.849 |
| (2 mg/kg/dose) | SD | N/A | 5.493 | 3.621 | 0.856 | 0.350 | 1.003 | 6.238 | 2.506 |
| | % CV | N/A | 33 | 24 | 7 | 3 | 6 | 30 | 18 |
| | N | 0 | 3 | 3 | 2 | 3 | 3 | 3 | 3 |
| | | | | | Day 13 | | | | |
| | Mean | BLOQ | 16.534 | 18.211 | 14.094 | 15.389 | 23.916 | 27.988 | 37.786* |
| | SD | N/A | 0.450 | 3.326 | 1.372 | 3.575 | 2.707 | 9.097 | 8.818 |
| | % CV | N/A | 3 | 18 | 10 | 23 | 11 | 33 | 23 |
| | N | 0 | 3 | 3 | 3 | 3 | 3 | 3 | 3 |
| | | | | | Day 41 | | | | |

TABLE 7-continued

| | | Sampling Time | | | | | | | |
| | | | Time Post Dosing Relative to Pre-dose | | | | | | |
| Group | | Pre-dose | 30 min | 1 hr | 2 hr | 4 hr | 8 hr | 12 hr | 24 hr |
|---|---|---|---|---|---|---|---|---|---|
| | Mean | 185.906 | 100.112 | 195.411 | 100.134 | 212.986 | 127.257 | 296.145 | 127.434 |
| | SD | 264.656 | 138.637 | 253.419 | 137.944 | 280.436 | 166.411 | 411.433 | 161.438 |
| | % CV | 142 | 138 | 130 | 138 | 132 | 131 | 139 | 127 |
| | N | 3 | 3 | 3 | 3 | 3 | 3 | 3 | 3 |

BLOQ—Below the limit of quantitation, <10 ng/mL; N represents the number of rats reporting with RTD-1 concentrations above the limit of quantitation.
Values are presented as the mean ± SD of N = 3 and the average ± the range of N = 2.
For N = 3, bold values are significantly different from Day 1; pair-wise comparison, p < 0.05 Student's t-test.
N/A—not applicable.

TABLE 8

| | | Sampling Time | | | | | | | |
| | | | Time Post Dosing Relative to Pre-dose | | | | | | |
| Group | | Pre-dose | 30 min | 1 hr | 2 hr | 4 hr | 8 hr | 12 hr | 24 hr |
|---|---|---|---|---|---|---|---|---|---|
| 4-TK ORTD-1 | | | | | Day 1 | | | | |
| High Dose | Mean | BLOQ | 19.827 | 17.019 | 14.163 | 23.085 | 27.873 | 37.129* | 36.851 |
| (4 mg/kg/dose) | SD | N/A | 4.754 | 5.943 | 2.337 | 3.617 | 5.989 | 10.687 | 8.741 |
| | % CV | N/A | 24 | 35 | 16 | 16 | 21 | 29 | 24 |
| | N | 0 | 3 | 3 | 3 | 3 | 3 | 3 | 3 |
| | | | | | Day 13 | | | | |
| | Mean | 56.688 | 23.650* | 109.634 | 19.566* | 106.184 | 45.219 | 177.471 | 51.198 |
| | SD | 66.312 | 2.089 | 135.109 | 1.845 | 131.529 | 14.302 | 207.364 | 21.121 |
| | % CV | 117 | 9 | 123 | 9 | 124 | 32 | 117 | 41 |
| | N | 3 | 3 | 3 | 3 | 3 | 3 | 3 | 3 |
| | | | | | Day 41 | | | | |
| | Mean | 171.510 | 234.782 | 225.608 | 194.810 | 210.728 | 214.045 | 305.575 | 263.958 |
| | SD | 120.089 | 319.717 | 159.433 | 270.617 | 150.795 | 267.542 | 263.070 | 352.308 |
| | % CV | 70 | 136 | 71 | 139 | 72 | 125 | 86 | 133 |
| | N | 3 | 3 | 3 | 3 | 3 | 3 | 3 | 3 |

BLOQ—Below the limit of quantitation, <10 ng/mL; N represents the number of rats reporting with RTD-1 concentrations above the limit of quantitation.
Values are presented as the mean ± SD of N = 3 and the average ± the range of N = 2.
For N = 3, bold values are significantly different from Day 1; pair-wise comparison. p < 0.05 Student's t-test.
N/A—not applicable.

Table 9 shows typical results for dose proportionality in regard to $C_{max}$ and $AUC_{0-TLast}$ for male and female rats.

TABLE 9

| Dose Day | Dose Ratio Mid to Low Dose | Dose Ratio High to Low Dose | $C_{max}$ Ratio Mid to Low Dose | $C_{max}$ Ratio High to Low Dose | $AUC_{0-TLast}$ Ratio Mid to Low Dose | $AUC_{0-TLast}$ Ratio High to Low Dose |
|---|---|---|---|---|---|---|
| | | | RTD-1, Male | | | |
| Day 1 | 2 | 4 | 1.78 | 1.90 | 2.01 | 2.84 |
| Day 13 | | | 0.39 | 0.73 | 0.54 | 0.82 |
| Day 41 | | | 1.26 | 2.64 | 1.60 | 3.75 |
| | | | RTD-1, Female | | | |
| Day 1 | 2 | 4 | 1.11 | 1.96 | 1.12 | 2.08 |
| Day 13 | | | 0.39 | 1.82 | 0.52 | 1.95 |
| Day 41 | | | 1.67 | 1.73 | 2.19 | 2.88 |

Figure 7A:
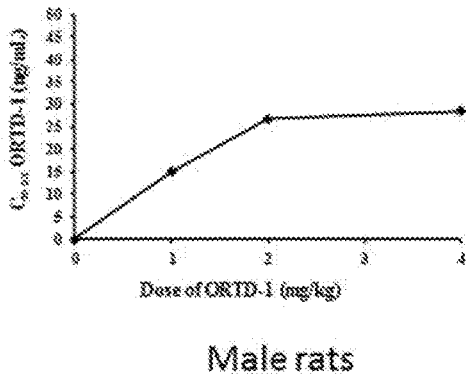
FIGS. 7A and 7B.
Figure 7B:
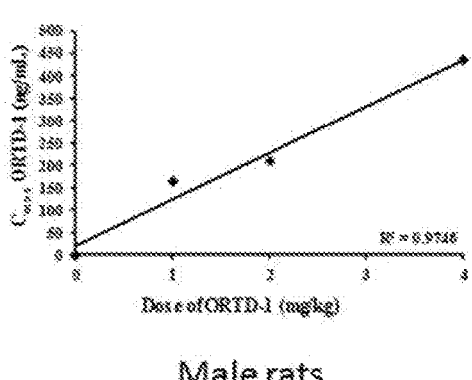
Figure 7B:
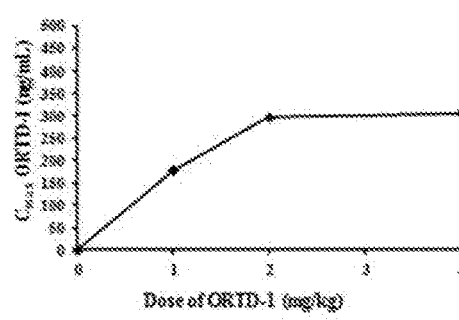
Figure 8A:
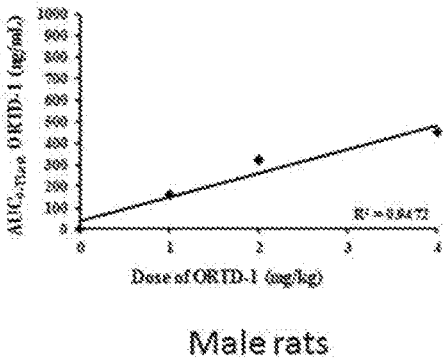
FIGS. 8A and 8B.
Figure 8A:
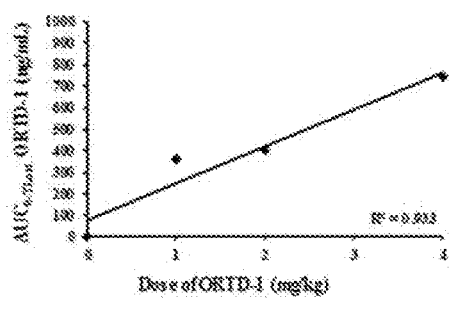
Figure 8B:
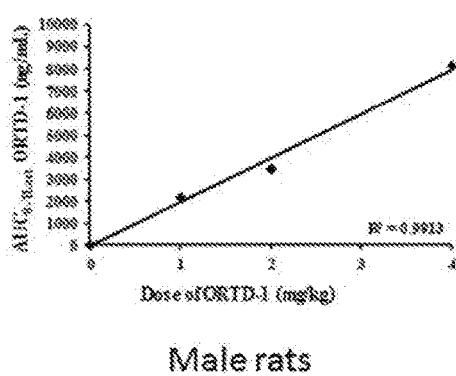
Figure 8B:
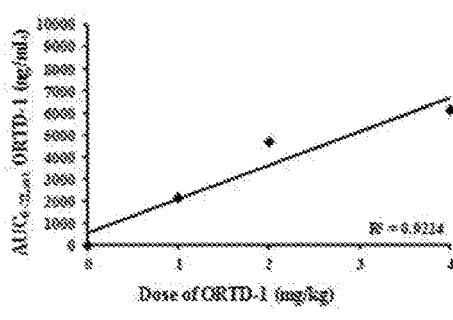

FIG. 7A provides a graph depicting results of a $C_{max}$ vs. θ-defensin dose linearity study for male and female rats at day 1. FIG. 7B provides a graph depicting results of a $C_{max}$ vs. θ-defensin dose linearity study for male and female rats at day 41. FIG. 8A provides a graph depicting results of an $AUC_{0-TLast}$ vs. θ-defensin dose linearity study for male and female rats at day 1. FIG. 8B provides a graph depicting results of an $AUC_{0-TLast}$ vs. θ-defensin dose linearity study for male and female rats at day 41.

Human Clinical Trials

Figure 9:
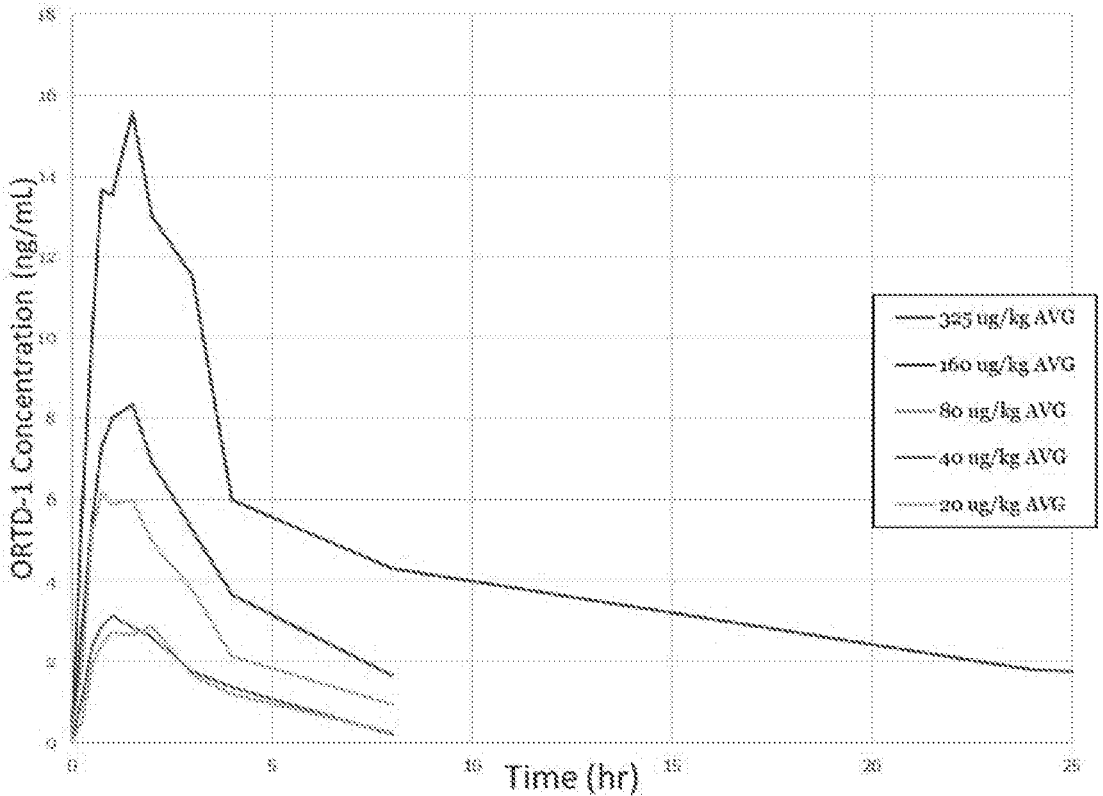
FIG. 9.
Figure 10A:
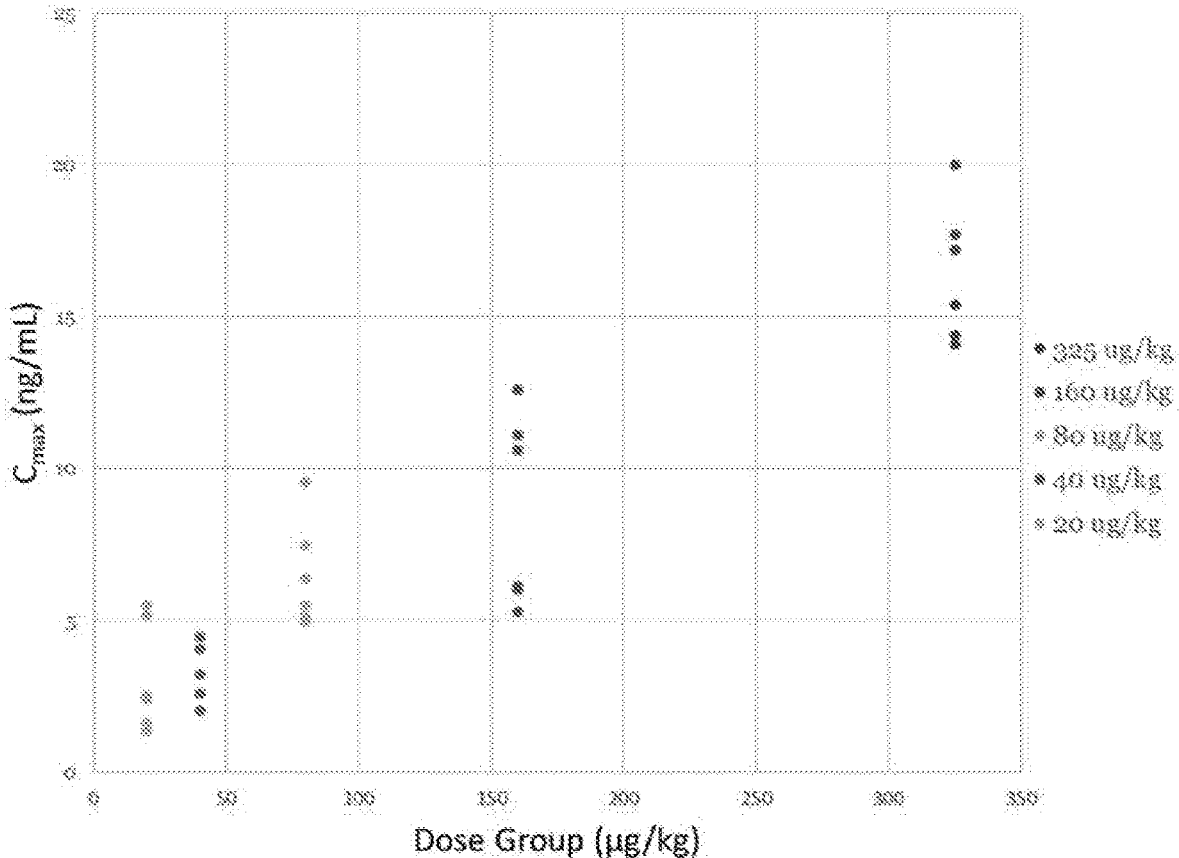
FIGS. 10A and 10B.
Figure 10B:
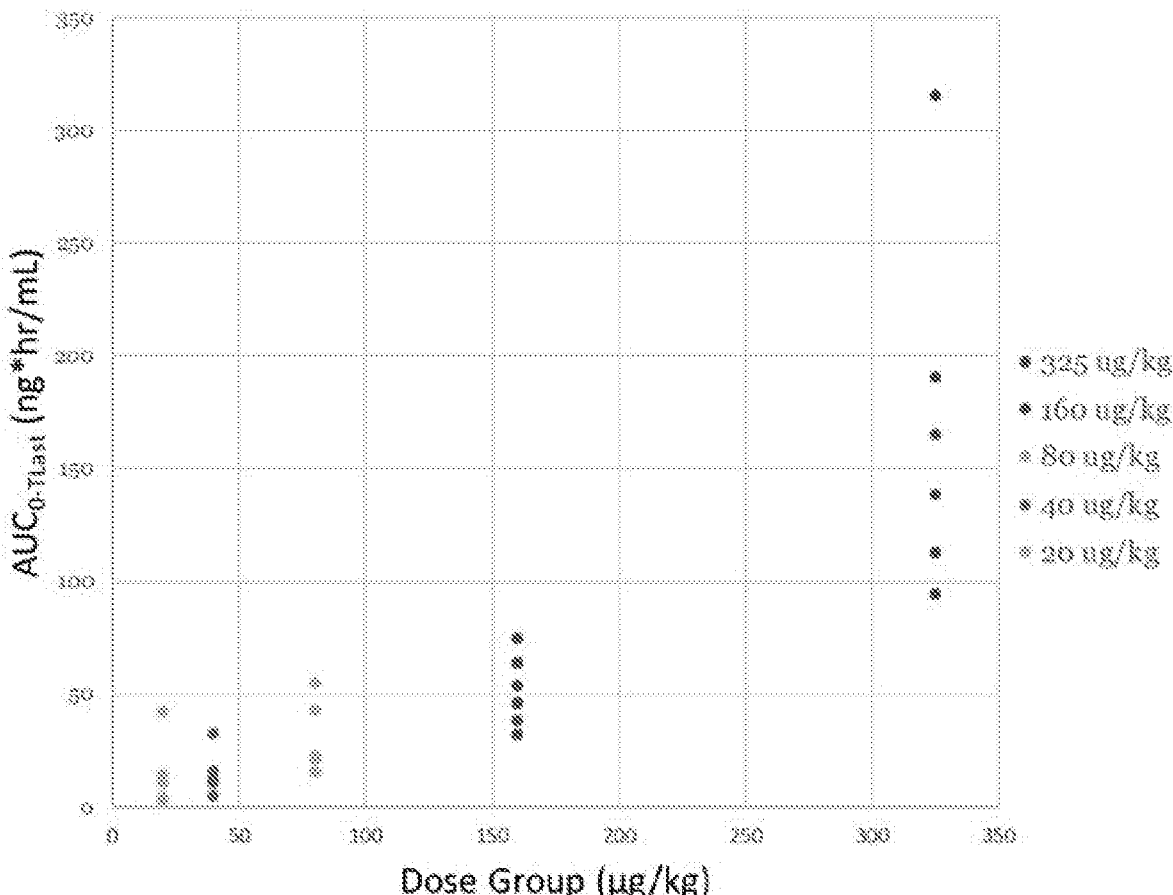
Figure 11A:
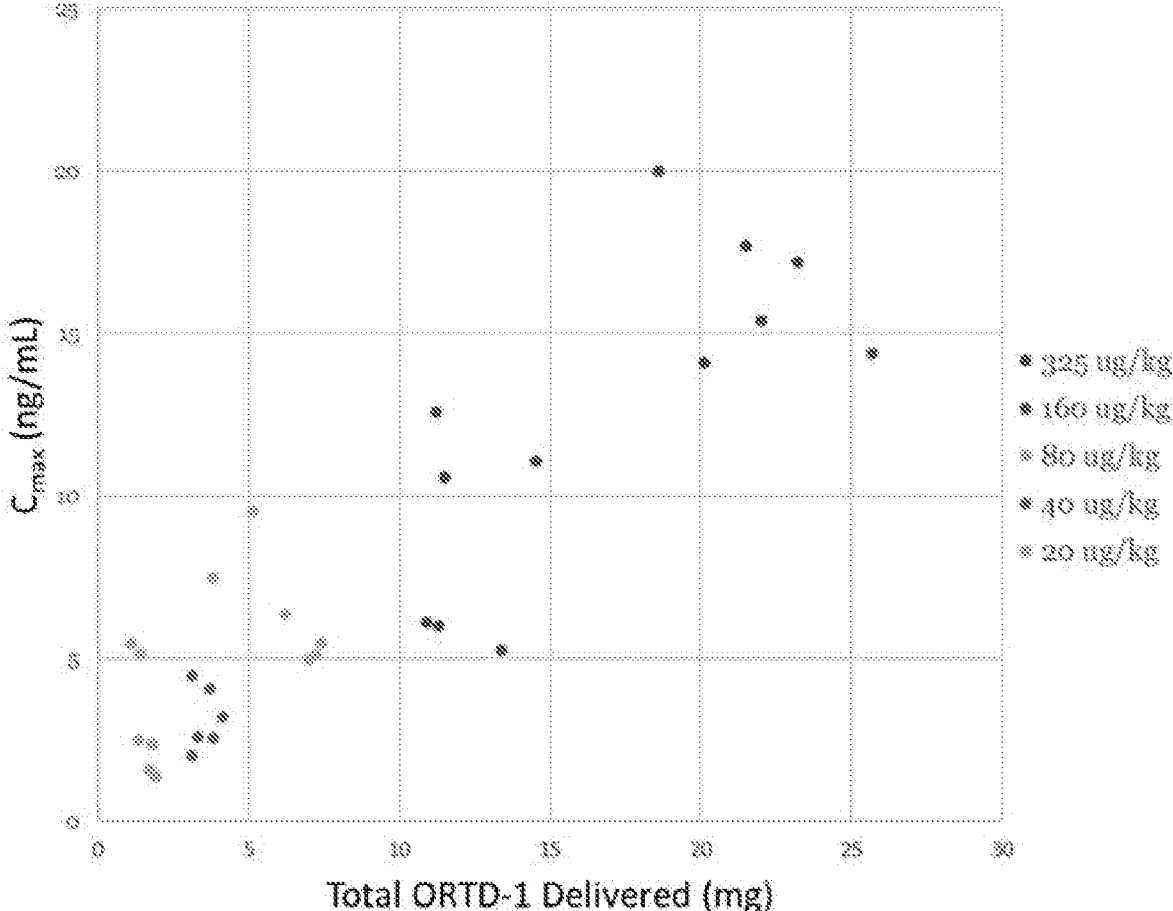
FIGS. 11A and 11B.
Figure 11B:
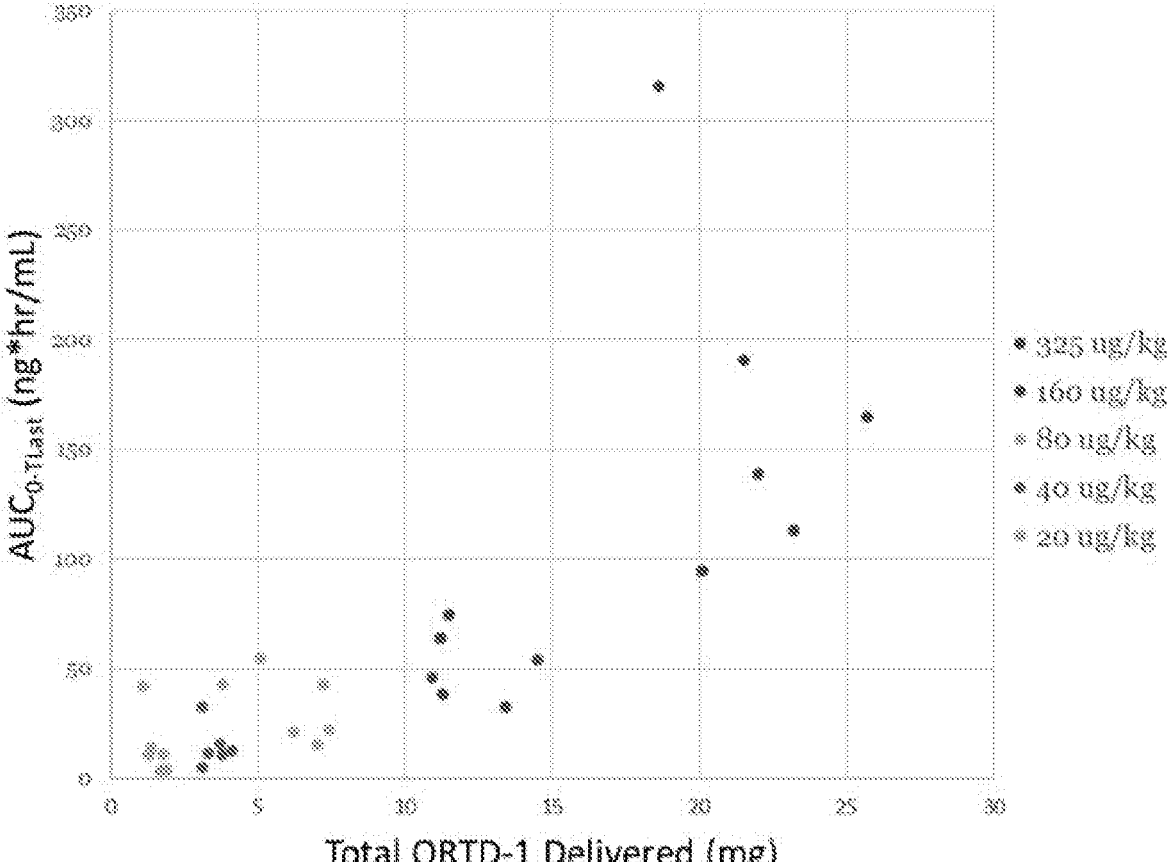

The θ-defensin RTD-1 was formulated in a mildly acidic buffer containing propylene glycol as described above, and administered subcutaneously to male and female subjects ranging in age from 23 to 73 followed by determination of plasma levels of the θ-defensin. Subjects received a θ-defensin of 20 μg/kg, 40 μg/kg, 80 μg/kg, 160 μg/kg, or 325 μg/kg by subcutaneous injection. It should be appreciated that these doses are, relatively, substantially smaller than those used in the animal studies described above. Subjects receiving 20 to 80 μg/kg received doses delivered at a single site. Subjects receiving larger amounts received their doses distributed between two sites. FIG. 9 shows typical results for measurement of θ-defensin concentration (ng/mL) in plasma over time for the different treatment groups. As shown, bioavailability on subcutaneous injection is dramatically increased in humans relative to rats. Similarly improved results for human subjects were noted relative to canine and porcine animal models of subcutaneous injection with RTD-1. The dependence of $C_{max}$ (ng/mL) on RTD-1 dose (μg/kg) is shown in FIG. 10A. Results of a similar study of dependence of $AUC_{0\text{-}TLast}$ on RTD-1 dose (μg/kg) is shown in FIG. 10B. The dependence of $C_{max}$ (ng/mL) on total RTD-1 administered (mg) is shown in FIG. 11A. Results of a similar study of dependence of $AUC_{0\text{-}TLast}$ on total RTD-1 administered (mg) is shown in FIG. 10B. Both $AUC_{0\text{-}TLast}$ and $C_{max}$ are approximately linear functions of the θ-defensin dose. Remarkably, far lower doses of the θdefensin are required to reach similar plasma concentrations in humans than were noted in test animals. Inventors anticipate that similar or improved results will be observed with analogs of θ-defensin.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refer to at least one of something selected from the group consisting of A, B, C . . . and N, the text should be interpreted as requiring only one element from the group, not A plus N, or B plus N, etc. filtration.

---

What is claimed is:

1. A pharmaceutical composition for treatment of a chronic inflammatory condition, comprising:

RTD-1 in an aqueous solution comprising 0.5% to 1.5% v/v propylene glycol, wherein the pharmaceutical composition has a pH of from 6.0 to 7.0 and is formulated for parenteral administration; wherein the 0.5% to 1.5% v/v propylene glycol increases the in vivo potency of RTD-1.

2. The pharmaceutical composition of claim 1, wherein RTD-1 is at a concentration of up to 20 mgmL$^{-1}$.

3. The pharmaceutical composition of claim 1, further comprising an acetate salt.

4. The pharmaceutical composition of claim 1, wherein the concentration of RTD-1 is selected such that pharmacologic potency of RTD-1 is increased by at least 10-fold relative to a similar concentration of RTD-1 provided in a normal saline solution.

5. The pharmaceutical composition of claim 1, wherein the concentration of RTD-1 is selected such that pharmacologic potency of RTD-1 is increased by at least 40-fold relative to a similar concentration of RTD-1 provided in a normal saline solution.

6. The pharmaceutical composition of claim 1, wherein the chronic inflammatory condition is selected from the group consisting of rheumatoid arthritis, inflammatory bowel disease, inflammation associated with cancer, diabetes, and a chronic disease characterized by dysregulated or unresolved chronic inflammation.

7. The pharmaceutical composition of claim 1, wherein the pharmaceutical composition comprises 1% v/v propylene glycol.

8. The pharmaceutical composition of claim 1, wherein the pharmaceutical composition comprises 20 mM acetate.

9. The pharmaceutical composition of claim 1, wherein the pharmaceutical composition has a pH of 6.5.

10. The pharmaceutical composition of claim 1, wherein RTD-1 is at a concentration of up to 10 mgmL$^{-1}$.

11. A method of treating an individual with a chronic inflammatory condition, comprising:

administering the pharmaceutical composition in any one of claims 1-10 to the individual in need of treatment.

* * * * *

SEQUENCE LISTING

```
<160> NUMBER OF SEQ ID NOS: 19

<210> SEQ ID NO 1
<211> LENGTH: 18
<212> TYPE: PRT
<213> ORGANISM: Macaca mulatta

<400> SEQUENCE: 1

Gly Phe Cys Arg Cys Leu Cys Arg Arg Gly Val Cys Arg Cys Ile Cys
1               5                   10                  15

Thr Arg

<210> SEQ ID NO 2
<211> LENGTH: 18
<212> TYPE: PRT
<213> ORGANISM: Macaca mulatta

<400> SEQUENCE: 2

Gly Val Cys Arg Cys Leu Cys Arg Arg Gly Val Cys Arg Cys Leu Cys
1               5                   10                  15

Arg Arg

<210> SEQ ID NO 3
<211> LENGTH: 18
<212> TYPE: PRT
<213> ORGANISM: Macaca mulatta

<400> SEQUENCE: 3

Gly Phe Cys Arg Cys Ile Cys Thr Arg Gly Phe Cys Arg Cys Ile Cys
1               5                   10                  15

Thr Arg

<210> SEQ ID NO 4
<211> LENGTH: 18
<212> TYPE: PRT
<213> ORGANISM: Macaca mulatta

<400> SEQUENCE: 4

Gly Ile Cys Arg Cys Ile Cys Thr Arg Gly Phe Cys Arg Cys Ile Cys
```

```
1               5               10              15

Val Leu

<210> SEQ ID NO 5
<211> LENGTH: 18
<212> TYPE: PRT
<213> ORGANISM: Macaca mulatta

<400> SEQUENCE: 5

Gly Ile Cys Arg Cys Leu Cys Arg Arg Gly Val Cys Arg Cys Ile Cys
1               5               10              15

Val Leu

<210> SEQ ID NO 6
<211> LENGTH: 18
<212> TYPE: PRT
<213> ORGANISM: Macaca mulatta

<400> SEQUENCE: 6

Gly Ile Cys Arg Cys Ile Cys Val Leu Gly Ile Cys Arg Cys Ile Cys
1               5               10              15

Val Leu

<210> SEQ ID NO 7
<211> LENGTH: 18
<212> TYPE: PRT
<213> ORGANISM: Papio anubis

<400> SEQUENCE: 7

Cys Val Cys Arg Arg Gly Val Cys Arg Cys Val Cys Thr Arg Gly Phe
1               5               10              15

Cys Arg

<210> SEQ ID NO 8
<211> LENGTH: 18
<212> TYPE: PRT
<213> ORGANISM: Papio anubis

<400> SEQUENCE: 8

Cys Val Cys Arg Arg Gly Val Cys Arg Cys Val Cys Arg Arg Gly Val
1               5               10              15

Cys Arg

<210> SEQ ID NO 9
<211> LENGTH: 18
<212> TYPE: PRT
<213> ORGANISM: Papio anubis

<400> SEQUENCE: 9

Cys Ile Cys Leu Leu Gly Ile Cys Arg Cys Val Cys Thr Arg Gly Phe
1               5               10              15

Cys Arg

<210> SEQ ID NO 10
<211> LENGTH: 18
<212> TYPE: PRT
<213> ORGANISM: Papio anubis

<400> SEQUENCE: 10

Cys Ile Cys Leu Leu Gly Ile Cys Arg Cys Val Cys Arg Arg Gly Val
1               5               10              15
```

-continued

Cys Arg

<210> SEQ ID NO 11
<211> LENGTH: 18
<212> TYPE: PRT
<213> ORGANISM: Papio anubis

<400> SEQUENCE: 11

Cys Ile Cys Leu Leu Gly Ile Cys Arg Cys Val Cys Arg Arg Gly Val
1               5                   10                  15

Cys Arg

<210> SEQ ID NO 12
<211> LENGTH: 18
<212> TYPE: PRT
<213> ORGANISM: Papio anubis

<400> SEQUENCE: 12

Cys Ile Cys Leu Leu Gly Ile Cys Arg Cys Ile Cys Leu Leu Gly Ile
1               5                   10                  15

Cys Arg

<210> SEQ ID NO 13
<211> LENGTH: 18
<212> TYPE: PRT
<213> ORGANISM: Papio anubis

<400> SEQUENCE: 13

Cys Phe Cys Arg Arg Gly Val Cys Arg Cys Val Cys Thr Arg Gly Phe
1               5                   10                  15

Cys Arg

<210> SEQ ID NO 14
<211> LENGTH: 18
<212> TYPE: PRT
<213> ORGANISM: Papio anubis

<400> SEQUENCE: 14

Cys Phe Cys Arg Arg Gly Val Cys Arg Cys Val Cys Arg Arg Gly Val
1               5                   10                  15

Cys Arg

<210> SEQ ID NO 15
<211> LENGTH: 18
<212> TYPE: PRT
<213> ORGANISM: Papio anubis

<400> SEQUENCE: 15

Cys Phe Cys Arg Arg Gly Val Cys Arg Cys Ile Cys Leu Leu Gly Ile
1               5                   10                  15

Cys Arg

<210> SEQ ID NO 16
<211> LENGTH: 18
<212> TYPE: PRT
<213> ORGANISM: Papio anubis

<400> SEQUENCE: 16

Cys Phe Cys Arg Arg Gly Val Cys Arg Cys Phe Cys Phe Phe Gly Val
1               5                   10                  15

-continued

```
Cys Arg

<210> SEQ ID NO 17
<211> LENGTH: 14
<212> TYPE: PRT
<213> ORGANISM: Artificial Sequence
<220> FEATURE:
<223> OTHER INFORMATION: synthetic cyclic theta defensin analog RTD-1-27

<400> SEQUENCE: 17

Gly Phe Cys Arg Cys Arg Arg Gly Val Cys Arg Cys Thr Arg
1               5                   10

<210> SEQ ID NO 18
<211> LENGTH: 14
<212> TYPE: PRT
<213> ORGANISM: Artificial Sequence
<220> FEATURE:
<223> OTHER INFORMATION: synthetic cyclic theta defensin analog RTD-1-28

<400> SEQUENCE: 18

Gly Val Cys Ile Val Arg Arg Arg Phe Cys Leu Cys Arg Arg
1               5                   10

<210> SEQ ID NO 19
<211> LENGTH: 14
<212> TYPE: PRT
<213> ORGANISM: Artificial Sequence
<220> FEATURE:
<223> OTHER INFORMATION: synthetic cyclic theta defensin analog RTD-1-29

<400> SEQUENCE: 19

Gly Val Cys Leu Cys Ile Arg Gly Arg Cys Arg Cys Arg Arg
1               5                   10
```